US009345691B2

(12) United States Patent
Cohen et al.

(10) Patent No.: US 9,345,691 B2
(45) Date of Patent: May 24, 2016

(54) BETA-LACTAM COMPOUNDS FOR ENHANCING T CELL-MEDIATED IMMUNE RESPONSES

(71) Applicant: STEM CELL MEDICINE LTD., Jerusalem (IL)

(72) Inventors: Irun R. Cohen, Rehovot (IL); Felix Mor, Kfar Saba (IL)

(73) Assignee: STEM CELL MEDICINE LTD., Jerusalem (IL)

(*) Notice: Subject to any disclaimer, the term of this patent is extended or adjusted under 35 U.S.C. 154(b) by 0 days.

(21) Appl. No.: 14/346,209

(22) PCT Filed: Sep. 20, 2012

(86) PCT No.: PCT/IL2012/050379
§ 371 (c)(1),
(2) Date: Mar. 20, 2014

(87) PCT Pub. No.: WO2013/042122
PCT Pub. Date: Mar. 28, 2013

(65) Prior Publication Data
US 2014/0227316 A1    Aug. 14, 2014

Related U.S. Application Data

(60) Provisional application No. 61/537,096, filed on Sep. 21, 2011.

(51) Int. Cl.
| | | |
|---|---|---|
| *A61K 39/00* | (2006.01) | |
| *C12N 5/00* | (2006.01) | |
| *C12N 5/02* | (2006.01) | |
| *A61K 39/395* | (2006.01) | |
| *A61K 35/00* | (2006.01) | |
| *C12N 5/071* | (2010.01) | |
| *C12N 5/07* | (2010.01) | |
| *C12N 5/16* | (2006.01) | |
| *A61K 31/43* | (2006.01) | |
| *A61K 45/06* | (2006.01) | |
| *A61K 31/431* | (2006.01) | |
| *A61K 47/48* | (2006.01) | |
| *A61K 31/546* | (2006.01) | |
| *A61K 35/17* | (2015.01) | |
| *A61K 31/424* | (2006.01) | |
| *A61K 38/00* | (2006.01) | |

(52) U.S. Cl.
CPC ............. *A61K 31/43* (2013.01); *A61K 31/424* (2013.01); *A61K 31/431* (2013.01); *A61K 31/546* (2013.01); *A61K 35/17* (2013.01); *A61K 39/0011* (2013.01); *A61K 45/06* (2013.01); *A61K 47/48284* (2013.01); *A61K 38/00* (2013.01); *C12N 5/0031* (2013.01); *C12N 2500/84* (2013.01); *C12N 2501/23* (2013.01); *C12N 2501/39* (2013.01)

(58) Field of Classification Search
CPC .. A61K 38/00; C12N 2500/84; C12N 5/0031; C12N 2501/23; C12N 2501/39
See application file for complete search history.

(56) References Cited

U.S. PATENT DOCUMENTS

| | | | |
|---|---|---|---|
| 6,015,809 A | 1/2000 | Zhu et al. | |
| 6,130,087 A * | 10/2000 | Srivastava et al. | ......... 435/372.3 |
| 6,610,681 B1 | 8/2003 | Koppel | |
| 6,627,625 B1 | 9/2003 | Koppel | |
| 2004/0110290 A1* | 6/2004 | June et al. | ...................... 435/372 |
| 2006/0160787 A1 | 7/2006 | Dou et al. | |

FOREIGN PATENT DOCUMENTS

| | | |
|---|---|---|
| CN | 101524517 A | 9/2009 |
| EP | 1864995 A1 | 12/2007 |
| KR | 20070025135 A | 3/2007 |
| LV | 12403 A | 12/1999 |
| WO | 94/18164 A1 | 8/1994 |
| WO | 97/21675 A1 | 6/1997 |
| WO | 99/24613 A1 | 5/1999 |
| WO | 01/12184 A1 | 2/2001 |
| WO | 03/061605 A2 | 7/2003 |
| WO | 2005/121148 A2 | 12/2005 |
| WO | 2007/099396 A2 | 9/2007 |
| WO | 2010/057647 A2 | 5/2010 |
| WO | 2011/047153 A1 | 4/2011 |
| WO | 2012/103456 A2 | 8/2012 |
| ZA | 1994/00128 | 8/1994 |

OTHER PUBLICATIONS

Spanou et al., J Am Soc Nephrol, 2006; 17: 2919-2927.*
Achiron et al., (2004) Blood transcriptional signatures of multiple sclerosis: unique gene expression of disease activity. Ann Neurol 55(3): 410-417.
Bertucci et al., (2001) Binding properties of human albumin modified by covalent binding of penicillin. Biochim Biophys Acta 1544(1-2): 386-392.
Bluestone et al., (2010) Genetics, pathogenesis and clinical interventions in type 1 diabetes. Nature 464(7293): 1293-1300.
Brundula et al., (2002) Targeting leukocyte MMPs and transmigration: minocycline as a potential therapy for multiple sclerosis. Brain 125(Pt 6): 1297-1308.
Cairo and Lucchini (1993) Molecular basis of reduced albumin gene expression in hepatoma cell lines with different growth rates. Exp Cell Res 206(2): 255-260.
Chen et al., (1994) Tumor immunogenicity determines the effect of B7 costimulation on T cell-mediated tumor immunity. J Exp Med 179(2): 523-532.

(Continued)

*Primary Examiner* — Gary Nickol
*Assistant Examiner* — Lakia Tongue
(74) *Attorney, Agent, or Firm* — Rothwell, Figg, Ernst & Manbeck P.C.

(57) ABSTRACT

Compositions and methods are provided, comprising at least one beta-lactam compound selected from the group consisting of cefuroxime, a penicillin, ceftriaxone, clavulanic acid, 6-aminopenicillanic acid (6-APA) and tazobactam, for enhancing T cell mediated immune responses in a subject, such as anti-tumor and anti-viral immune responses.

12 Claims, 11 Drawing Sheets

(56) References Cited

OTHER PUBLICATIONS

Choi et al., (2003) Effect of moxifloxacin on production of proinflammatory cytokines from human peripheral blood mononuclear cells. Antimicrob Agents Chemother 47(12): 3704-3707.
Christie et al., (1987) Drug-protein conjugates—XIII. The disposition of the benzylpenicilloyl hapten conjugated to albumin. Biochem Pharmacol 36(20): 3379-3385.
Cornman (1944) A selective lethal effect of penicillin on sarcoma cells growing with normal tissue in roller tube cultures. J Gen Physiol 28(2): 113-118.
de Haan et al., (1985) Three epitope-specific monoclonal antibodies against the hapten penicillin. Int Arch Allergy Appl Immunol 76(1): 42-46.
Di Marco et al., (2001) Sodium fusidate (fusidin) ameliorates the course of monophasic experimental allergic encephalomyelitis in the Lewis rat. Mult Scler 7(2): 101-104.
Elias et al., (1997) Hsp60 peptide therapy of NOD mouse diabetes induces a Th2 cytokine burst and downregulates autoimmunity to various beta-cell antigens. Diabetes 46(5): 758-764.
Garren et al., (2001) Combination of gene delivery and DNA vaccination to protect from and reverse Th1 autoimmune disease via deviation to the Th2 pathway. Immunity 15(1): 15-22.
Giuliani et al., (2005) Effective combination of minocycline and interferon-beta in a model of multiple sclerosis. J Neuroimmunol 165(1-2): 83-91.
Gollapudi et al., (2003) Molecular basis of rifampicin-induced inhibition of anti-CD95-induced apoptosis of peripheral blood T lymphocytes: the role of CD95 ligand and FLIPs. J Clin Immunol 23(1): 11-22.
Gorelik et al., (1980) Control of lung metastasis progression in mice: role of growth kinetics of 3LL Lewis lung carcinoma and host immune reactivity. J Natl Cancer Inst 65(6): 1257-1264.
Ishimatsu et al., (2004) Macrolide antibiotics induce apoptosis of human peripheral lymphocytes in vitro. Int J Antimicrob Agents 24(3): 49-55.
Kadota et al., (2005) Antibiotic-induced apoptosis in human activated peripheral lymphocytes. Int J Antimicrob Agents 25(3): 216-220.
Keymeulen et al., (2010) Transient Epstein-Barr virus reactivation in CD3 monoclonal antibody-treated patients. Blood 115(6): 1145-1155.
Kloppenburg et al., (1996) The tetracycline derivative minocycline differentially affects cytokine production by monocytes and T lymphocytes. Antimicrob Agents Chemother 40(4): 934-940.
Kolbach et al., (1995) Bullous pemphigoid successfully controlled by tetracycline and nicotinamide. Br J Dermatol 133 (1): 88-90.
Kong et al., (2009) A novel phosphorylated STAT3 inhibitor enhances T cell cytotoxicity against melanoma through inhibition of regulatory T cells. Cancer Immunol Immunother 58(7): 1023-1032.
Krakauer and Buckley (2003) Doxycycline is anti-inflammatory and inhibits staphylococcal exotoxin-induced cytokines and chemokines. Antimicrob Agents Chemother 47(11): 3630-3633.
Kratz (2008) Albumin as a drug carrier: design of prodrugs, drug conjugates and nanoparticles. J Control Release 132 (3): 171-183.
Kuhn et al., (2004) Beta-lactams and their potential use as novel anticancer chemotherapeutics drugs. Front Biosci 9: 2605-2617.
Lewis (1944) The failure of purified penicillin to retard the growth of grafts of sarcoma in mice. Science 100(2597): 314-315.
Li et al., (2001) Immune response against 3LL Lewis lung carcinoma potentiates the therapeutic efficacy of endostatin. J Immunother 24(6): 472-481.
Liu et al., (1998) TNF is a potent anti-inflammatory cytokine in autoimmune-mediated demyelination. Nat Med 4(1): 78-83.
Masharani and Becker (2010) Teplizumab therapy for type 1 diabetes. Expert Opin Biol Ther 10(3): 459-465.
Melzer et al., (2008) A beta-lactam antibiotic dampens excitotoxic inflammatory CNS damage in a mouse model of multiple sclerosis. PLoS One 3(9): e3149, 12 pages.
Mimran et al., (2004) DNA vaccination with CD25 protects rats from adjuvant arthritis and induces an antiergotypic response. J Clin Invest 113(6): 924-932.
Mor and Cohen (1993) Shifts in the epitopes of myelin basic protein recognized by Lewis rat T cells before, during, and after the induction of experimental autoimmune encephalomyelitis. J Clin Invest 92(5): 2199-2206.
Mor et al., (1990) Clinical modeling of T cell vaccination against autoimmune diseases in rats. Selection of antigen-specific T cells using a mitogen. J Clin Invest 85(5): 1594-1598.
Mor et al., (2005) Identification of aldolase as a target antigen in Alzheimer's disease. J Immunol 175(5): 3439-3445.
Nieuwenhuis et al., (2000) Oral antibiotics as a novel therapy for arthritis: evidence for a beneficial effect of intestinal *Escherichia coli*. Arthritis Rheum 43(11): 2583-2589.
Popovic et al., (2002) Inhibition of autoimmune encephalomyelitis by a tetracycline. Ann Neurol 51(2): 215-223.
Rothstein et al., (2005) Beta-lactam antibiotics offer neuroprotection by increasing glutamate transporter expression. Nature 433(7021): 73-77.
Satoh et al., (2006) T cell gene expression profiling identifies distinct subgroups of Japanese multiple sclerosis patients. J Neuroimmunol 174(1-2): 108-118.
Brander et al., (1995) Heterogeneous T cell responses to beta-lactam-modified self-structures are observed in penicillin-allergic individuals. J Immunol 155: 2670-2678.
Cottagnoud et al., (1988) Inhibition of HSV-1 and vaccinia virus replication by cephalosporin derivatives. Antiviral Res 10: 59-70.
Mor et al., (2013) Beta-lactam antibiotics modulate T-cell functions and gene expression via covalent binding to cellular albumin. Proc Natl Acad Sci U S A 110(8): 2981-2986.
Grill and Maganti (2011) Neurotoxic effects associated with antibiotic use: management considerations. Br J Clin Pharmacol 72(3): 381-393.
Kosiewicz et al., (2011) Gut microbiota, immunity, and disease: a complex relationship. Front Microbiol 2: 180, 11 pages.
Kranich et al., (2011) Commensal flora and the regulation of inflammatory and autoimmune responses. Semin Immunol 23(2): 139-145.
Pásztói et al., (2011) Infection and autoimmunity: Lessons of animal models. Eur J Microbiol Immunol 1(3): 198-207.
Rolinson (1998) Forty years of beta-lactam research. J Antimicrob Chemother 41(6): 589-603.

\* cited by examiner

Protein View

Match to: ALBU_HUMAN Score: 114

Serum albumin precursor - Homo sapiens (Human)

Found in search of C:\Temp\mas502.tmp

Nominal mass ($M_r$): 69321; Calculated pI value: 5.92
NCBI BLAST search of ALBU_HUMAN against nr
Taxonomy: Homo sapiens
Variable modifications: Carbamidomethyl (C),Deamidated (NQ),Oxidation (M)
Cleavage by Trypsin: cuts C-term side of KR unless next residue is P
Sequence Coverage: 4%

Matched peptides shown in Bold Red

```
  1 MKWVTFISLL FLFSSAYSRG VFRRDAHKSE VAHRFKDLGE ENFKALVLIA
 51 FAQYLQQCPF EDHVKLVNEV TEFAKTCVAD ESAENCDKSL HTLFGDKLCT
101 VATLRETYGE MADCCAKQEP ERNECFLQHK DDNPNLPRLV RPEVDVMCTA
151 FHDNEETFLK KYLYEIARRH PYFYAPELLF FAKRYKAAFT ECCQAADKAA
201 CLLPKLDELR DEGKASSAKQ RLKCASLQKF GERAFKAWAV ARLSQRFPKA
251 EFAEVSKLVT DLTKVHTECC HGDLLECADD RADLAKYICE NQDSISSKLK
301 ECCEKPLLEK SHCIAEVEND EMPADLPSLA ADFVESKDVC KNYAEAKDVF
351 LGMFLYEYAR RHPDYSVVLL LRLAKTYETT LEKCCAAADP HECYAKVFDE
401 FKPLVEEPQN LIKQNCELFE QLGEYKFQNA LLVRYTKKVP QVSTPTLVEV
451 SRNLGKVGSK CCKHPEAKRM PCAEDYLSVV LNQLCVLHEK TPVSDRVTKC
501 CTESLVNRRP CFSALEVDET YVPKEFNAET FTFHADICTL SEKERQIKKQ
551 TALVELVKHK PKATKEQLKA VMDDFAAFVE KCCKADDKET CFAEEGKKLV
601 AASQAALGL
```

(SEQ ID NO: 19)

FIGURE 2B

1= Thymus  5= Intestine
2= Spleen  6= Liver
3= Serum   7= Lung
4= Kidney  8= hPBL PC 1= mouse Mesenchymal stem cells  5= human ALL line MOLT-4
2= mouse Immature dendritic cells  6= rat hepatoma line FAO
3= mouse Mature dendritic cells  7= human ALL line CEM
4= human T cell leukemia Jurkat 1= NC
2= Cyto-hAlb-Pen 1hr
3= Cyto-hAlb-Pen 2hr
4= Cyto-hAlb-Pen 3hr
5= Cyto-Pen 3hr
6= Nucl-NC
7= Nucl-hAlb-Pen 1hr
8= Nucl-hAlb-Pen 2hr
9= Nucl-hAlb-Pen 3hr
10= Nucl Pen 3hr

SEQUENCE LISTING

<160> NUMBER OF SEQ ID NOS: 19

<210> SEQ ID NO 1
<211> LENGTH: 16
<212> TYPE: DNA
<213> ORGANISM: Artificial Sequence
<220> FEATURE:
<223> OTHER INFORMATION: Primer

<400> SEQUENCE: 1
cccgattact ccgtgt                                                     16

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
tggcgttttg gaatccata                                                  19

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
atgcgctatt agttcgttac                                                 20

<210> SEQ ID NO 4
<211> LENGTH: 16
<212> TYPE: DNA
<213> ORGANISM: Artificial Sequence
<220> FEATURE:
<223> OTHER INFORMATION: Primer

<400> SEQUENCE: 4
catggtcgcc tgttca                                                     16

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
tagctctagg agggctg                                                    17

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
accacaacca tgcctta                                                    17

<210> SEQ ID NO 7
<211> LENGTH: 16
<212> TYPE: DNA
<213> ORGANISM: Artificial Sequence

```
<220> FEATURE:
<223> OTHER INFORMATION: Primer

<400> SEQUENCE: 7
atctccgcgt aaggaa                                                    16

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
tgggactaac aatcgtg                                                   17

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
tcctagagac cctggtg                                                   17

<210> SEQ ID NO 10
<211> LENGTH: 17
<212> TYPE: DNA
<213> ORGANISM: Artificial Sequence
<220> FEATURE:
<223> OTHER INFORMATION: Primer

<400> SEQUENCE: 10
ggactgcgtg taagatg                                                   17

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
aggagtatta caccgtcaag                                                20

<210> SEQ ID NO 12
<211> LENGTH: 16
<212> TYPE: DNA
<213> ORGANISM: Artificial Sequence
<220> FEATURE:
<223> OTHER INFORMATION: Primer

<400> SEQUENCE: 12
gggttgggcc tatcat                                                    16

<210> SEQ ID NO 13
<211> LENGTH: 17
<212> TYPE: DNA
<213> ORGANISM: Artificial Sequence
<220> FEATURE:
<223> OTHER INFORMATION: Primer

<400> SEQUENCE: 13
acatcctgcg agactac                                                   17
```

-continued

<210> SEQ ID NO 14
<211> LENGTH: 16
<212> TYPE: DNA
<213> ORGANISM: Artificial Sequence
<220> FEATURE:
<223> OTHER INFORMATION: Primer

<400> SEQUENCE: 14
caccgcatac acactt                                                  16

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
cttctggagc ccattg                                                  16

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
acggtacatc cacgtag                                                 17

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
gactttgtgg tagaggca                                                18

<210> SEQ ID NO 18
<211> LENGTH: 16
<212> TYPE: DNA
<213> ORGANISM: Artificial Sequence
<220> FEATURE:
<223> OTHER INFORMATION: Primer

<400> SEQUENCE: 18
aaaacgtgga gtcagc                                                  16

<210> SEQ ID NO 19
<211> LENGTH: 609
<212> TYPE: PRT
<213> ORGANISM: Homo sapiens

<400> SEQUENCE: 19

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

-continued

```
Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480
```

-continued

```
Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu
```

BETA-LACTAM COMPOUNDS FOR ENHANCING T CELL-MEDIATED IMMUNE RESPONSES

CROSS REFERENCE TO RELATED APPLICATIONS

This application is a 35 U.S.C. §371 National Phase Entry Application from PCT/IL2012/050379, filed Sep. 20, 2012, and designating the United States, which claims the benefit of U.S. Patent Application No. 61/537,096 filed Sep. 21, 2011, which are incorporated herein in their entireties.

The present application includes a Sequence Listing filed in electronic format. The Sequence Listing is entitled "3596-164_ST25.txt" created on Oct. 22, 2015, and is 9,000 bytes in size. The information in the electronic format of the Sequence Listing is part of the present application and is incorporated herein by reference in its entirety.

FIELD OF THE INVENTION

The present invention relates to compositions and methods comprising beta-lactam compounds for enhancing T cell mediated immune responses, such as anti-tumor and anti-viral immune responses.

BACKGROUND OF THE INVENTION

Beta-lactam compounds are a group of chemical entities containing a beta-lactam ring, namely a cyclic amide composed of three carbon atoms and one nitrogen atom. The beta-lactam ring is part of the structure of several antibiotic families, the principal ones being the penicillins, cephalosporins, carbapenems and monobactams, which are therefore referred to as beta-lactam antibiotics. These antibiotics generally work by inhibiting bacterial cell wall synthesis, thereby leading to a weakened cell wall and osmotic lysis of the bacterial cell. Bacteria can, however, become resistant to beta-lactam antibiotics, for example, by producing enzymes which hydrolyze the beta-lactam moiety and render the antibiotic inactive. These enzymes are generally referred to as beta-lactamases.

Beta-lactam compounds also include compounds that do not have direct anti-bacterial activity, but function as inhibitors of beta-lactamase enzymes and are typically combined with beta-lactam antibiotics to overcome bacterial resistance to the antibiotics. Clinically approved beta-lactamase inhibitors include, for example, clavulanic acid, which is given in conjunction with amoxicillin or ticarcillin (belong to the penicillin family).

It was initially thought that beta-lactam antibiotics would not be able to directly affect mammalian cells, since mammalian cells do not produce cell walls. However, theoretically, beta-lactam compounds might bind eukaryotic cellular proteins and affect their functions. Indeed, screening of various compounds in models of amyotrophic lateral sclerosis led to the discovery that beta-lactam antibiotics could increase the expression of neuronal glutamate transporter in cultured mammalian cells. Moreover, ceftriaxone (of the cephalosporin family) was found to protect animals from several forms of glutamate-induced toxicity (Rothstein et al. (2005) Nature 433, 73-77).

Previous reports have addressed the possibility of penicillin binding to plasma proteins, which was suspected as the initial step in the sequence of events leading to adverse hypersensitivity reactions associated with this antibiotic. For example, Christie et al. (1987) Biochem Pharmacol, 36, 3379-3385 have synthesized a conjugate of albumin and benzylpenicillin (also known as penicillin G), and investigated its disposition and metabolism. Bertucci et al. (2001) Biochim Biophys Acta, 1544, 386-392 have studied structural and binding properties of albumin modified with penicillin G.

The conventional antibacterial properties of beta-lactam antibiotics are utilized in the treatment of cancer patients. Specifically, these compounds are often indicated for treating neutropenic cancer patients receiving chemotherapy or radiation therapy, which are prone to bacterial infections due to immunodeficiency.

Several classes of beta-lactam compounds have been shown to possess anti-cancer properties (reviewed in Kuhn et al. (2004) Front Biosci., 9:2605-17). For example, N-thiolated beta-lactam compounds, also referred to as N-thiolated monobactams, have been found to induce tumor cell apoptosis. The 4-alkylidene-betalactams have been shown to inhibit matrix metalloproteinases essential for tumor-induced neovascularization. Beta-lactam compounds with polyaromatic substituents have been shown to induce tumor cell death in a variety of cancer cell lines, and slow or inhibit tumor cell growth in vivo.

Cornman (1944) J Gen Physiol., 28(2):113-8 has reported about a selective lethal effect of an agent present in a penicillin preparation towards rat and mouse sarcoma cells, which was observed when these cells were grown with normal cells in tissue cultures. However, subsequent work (Lewis (1944) Science, 100; 314) has ruled out the involvement of penicillin in this effect, showing that it was not exerted by highly purified colorless penicillin, but rather due to some substance present in the less purified samples along with the bacteriostatic factor. Moreover, penicillin, as well as other beta-lactam antibiotics, is routinely and widely used in cell cultures, including cancer cell culture, to prevent bacterial contamination of the culture medium.

US 2006/0160787 discloses N-thiolated beta-lactam compounds and analogs and pharmaceutically acceptable salts, esters and amides thereof. US 2006/0160787 further discloses methods for inducing tumor cell death or inhibiting tumor cell proliferation, and methods for inducing DNA damage, inhibiting DNA replication, activating p38 MAP kinase, or activating caspase cascade activation, or releasing cytochrome C from mitochondria into the cytoplasm in a tumor cell. Methods for treating cancer using N-thiolated beta-lactam compounds, as well as pharmaceutical compositions comprising the same are further disclosed.

LV Patent Application No. 1998000000132 discloses pharmacologically active substances, particularly cytotoxic agents for chemotherapy for cancer. The compounds contain modified penicillin sulfoxide esters or penicillin sulfone esters having specifically selected substituents in position 6 and in the 2-beta-methylgroup.

WO 2007/099396 discloses a therapeutic kit to provide a safe and effective dosage of an antibiotic agent, and a foamable composition including an antibiotic agent, at least one organic carrier, a surface-active agent, at least one polymeric additive and water. WO 2007/099396 further discloses a method of treating, alleviating or preventing disorders of the skin, body cavity or mucosal surface, wherein the disorder involves inflammation as one of its etiological factors, including administering topically to a subject having the disorder, a foamed composition including: an antibiotic agent, inter alia beta-lactam antibiotics, at least one organic carrier, a surface-active agent, a polymeric additive and water. The antibiotic agent includes, inter alia, beta-lactam antibiotics.

U.S. Pat. No. 6,610,681 discloses therapeutic methods using clavulanic acid and related compounds, inter alia, a method for treating a prostate disease selected from prostate cancer and benign prostate hyperplasia in a human patient.

U.S. Pat. No. 6,627,625 discloses therapeutic methods using beta-lactam compounds including beta-lactam antibiotics and beta-lactamase inhibitors, inter alia, a method for treating a prostate disease selected from prostate cancer and benign prostate hyperplasia in a human patient.

Antibiotics not containing beta-lactam moieties have been previously reported to affect apoptosis and cytokine secretion by T cells. Moxifloxacin, a fluoroquinolone antibiotic, was reported to inhibit TNFα and IL-6 secretion by T cells (Choi et al. (2003) *Antimicrob Agents Chemother*, 47, 3704-3707). Rifampicin, an antibiotic drug of the rifamycin group, was found to inhibit CD95-induced apoptosis by T cells (Gollapudi et al. (2003) *J Clin Immunol*, 23, 11-22), and macrolide antibiotics were reported to induce apoptosis in T cells (Ishimatsu et al. (2004) *Int J Antimicrob Agents*, 24, 247-253; and Kadota et al. (2005) *Int J Antimicrob Agents*, 25, 216-220). Minocycline was found to inhibit TNFα and INFγ (Kloppenburg et al. (1996) *Antimicrob Agents Chemother*, 40, 934-940), and doxycycline demonstrated anti-inflammatory effects (Krakauer et al. (2003) *Antimicrob Agents Chemother*, 47, 3630-3633).

Previous work on the effects of antibiotics on experimental autoimmune diseases has shown that minocycline, fucidin and tetracycline could inhibit experimental autoimmune encephalomyelitis (EAE) (Giuliani et al. (2005) *J Neuroimmunol*, 165, 83-91; Brundula et al. (2002) *Brain*, 125, 1297-1308; Di Marco et al. (2001) *Mult Scler*, 7, 101-104; and Popovic et al. (2002) *Ann Neurol*, 51, 215-223). Oral vancomycin, which is poorly absorbed, was found to inhibit adjuvant arthritis by its effects on the intestinal flora (Nieuwenhuis et al. (2000) *Arthritis Rheum*, 43, 2583-2589). Tetracycline is used clinically as an immune modulator in patients with Pemphigus and Bullous Pemphigoid (Calebotta et al. (1999) *Int J Dermatol*, 38, 217-221; and Kolbach et al. (1995) *Br J Dermatol*, 133, 88-90).

WO 2003/061605 discloses methods for treating a host suffering from a chronic immune disease, e.g., multiple sclerosis or chronic fatigue syndrome. In practicing the subject methods, an effective amount of an elastase inhibitory agent, e.g., a beta-lactam containing compound, is administered to the host. Compositions for use in practicing the subject methods are also disclosed.

WO 1999/024613 reports a newly-identified human blood bacterium which appears to be directly or indirectly associated with several diseases such as chronic fatigue syndrome, multiple sclerosis and other autoimmune diseases. WO 1999/024613 discloses, inter alia, a method for treating a pathophysiological state in an individual having human blood bacterium in the blood, comprising the step of administering to said individual a therapeutically effective amount of at least one antibiotic selected from the group consisting of penicillin G, penicillin V, probenecid, Augmentin, dicloxacillin, Ciprofloxacin, Isoniazid, third-generation cephalosporins, azithromycin, clarithromycin, chloroquin, hydroxychloroquine, minocycline, doxycycline and primaquine.

Nowhere is it disclosed or suggested that certain beta-lactam compounds, including both antibiotics and beta-lactam compounds devoid of anti-bacterial effect, can directly and effectively stimulate T cell activity, and particularly that these beta-lactam compounds can augment tumor rejection. In addition, nowhere is it disclosed or suggested that a similar effect is observed when these beta-lactam compounds are conjugated to a protein, for example, to albumin. There is a medical need for compositions and methods that enhance T cell activity, which may be useful, for example, in cancer therapy.

SUMMARY OF THE INVENTION

The present invention provides compositions and methods useful for immunomodulation. More specifically, the present invention provides compositions and methods useful for enhancing T cell mediated immune responses in a subject, such as anti-tumor immune responses or anti-viral immune responses. The compositions and methods of the present invention utilize specific beta-lactam compounds that were surprisingly found to modulate T cells such that their activity is enhanced, and promote tumor rejection. The beta-lactam compounds exemplified according to the principles disclosed herein include cefuroxime, penicillin, ceftriaxone, clavulanic acid, 6-aminopenicillanic acid (6-APA) and tazobactam. In particular embodiments the compositions and methods are useful for enhancing cell mediated immune responses of the Th1 type and/or to down regulate cell mediated immune responses of the Th2 type.

The present invention is based in part on the unexpected finding that several commonly used beta-lactam antibiotics, as well as beta-lactam compounds devoid of antibacterial activity, promote tumor rejection in vivo. As exemplified hereinbelow, a significant inhibition of tumor growth was observed in a mouse lymphoma model upon administration of the beta-lactam compounds used according to the present invention. These compounds also have a beneficial effect on survival, as exemplified hereinbelow in a lung carcinoma model.

Additionally, these beta-lactam compounds were shown to increase the severity of experimental autoimmune encephalomyelitis (EAE) and/or adjuvant arthritis (AA) in rodents, as further exemplified hereinbelow. Gene expression analysis of human T cells upon incubation with the beta-lactam compounds show that these compounds induce changes in the expression of immune-related genes in the cells. Increasing evidence suggests that tumors can elicit an immune response, and that the immune system is involved in tumor rejection. Without wishing to be bound by any particular theory or mechanism of action, it is contemplated that administration of the beta-lactam compounds as disclosed herein induces an augmented T cell-mediated immune response, resulting in immune-mediated tumor rejection.

Advantageously, the beta-lactam antibiotics utilized in the compositions and methods of the present invention were found to induce their effect while administered in sub-antibacterial doses or sub-antibacterial treatment regimes, thus avoiding, in some embodiments, untoward effects on commensal bacteria and without selecting resistant bacteria. In addition, as noted above, the present invention may utilize beta-lactam compounds substantially devoid of antibacterial activity.

The present invention is further based on the finding that the immunomodulatory effect disclosed above is maintained when the beta-lactam compounds are attached to a protein, such as albumin, as exemplified herein below. Penicillin-modified albumin exhibits a longer half-life compared to free penicillin, therefore the use of a conjugate according to embodiments of the present invention may provide prolonged therapeutic effect. Thus, the present invention further provides compositions and methods that utilize albumin-beta-lactam conjugates or complexes.

According to one aspect, the present invention provides a method for enhancing a T cell mediated immune response in a subject, the method comprises administering to the subject a pharmaceutical composition comprising a beta-lactam compound or a salt thereof thereby enhancing a Th1 immune response in the subject and/or decreasing a Th2 immune response in the subject. Thus, the present invention provides a method for enhancing a T cell mediated immune response in a subject, the method comprising administering to the subject a pharmaceutical composition comprising a beta-lactam compound or a salt thereof selected from the group consisting of cefuroxime, a penicillin, ceftriaxone, clavulanic acid, 6-aminopenicillanic acid (6-APA) and tazobactam. Each possibility represents separate embodiment of the invention.

In some embodiments, the enhanced immune-response is a T cell mediated anti-tumor response.

In some embodiments, the method is utilized for cancer treatment.

In additional embodiments, the method is utilized for the treatment of viral infections.

In some embodiments, the administered pharmaceutical composition comprises a beta-lactam antibiotic, or a salt thereof, selected from the group consisting of cefuroxime, a penicillin and ceftriaxone. Each possibility represents a separate embodiment of the invention.

In some embodiments, the penicillin is selected from benzylpenicillin (also known as penicillin G) and phenoxymethylpenicillin (also known as penicillin V). In some specific embodiments, the penicillin is benzylpenicillin.

In some embodiments, the administered pharmaceutical composition comprises a sub-antibacterial dose of the beta-lactam antibiotic. According to these embodiments, the antibiotic is present in the composition in an amount which is lower than that required for producing an effective antibacterial activity in a subject. For example, the composition may comprise about 90% or less, about 80% or less, about 70% or less, about 60% or less, about 50% or less, about 40% or less, about 30% or less, about 20% or less, about 10% or less, or about 5% or less, of the antibacterial dose. Each possibility represents a separate embodiment of the invention.

In alternative or additional embodiments, the pharmaceutical composition comprising the beta-lactam antibiotic is administered in a sub-antibacterial treatment regime. According to these embodiments, the antibiotic is administered in a treatment regime which is different from the typical antibacterial treatment regime known for this antibiotic, such that substantially no antibacterial effect is provided. For example, in some embodiments, the antibiotic is administered fewer times per day compared to the antibacterial treatment regime. In some exemplary embodiments, the antibiotic is administered in a frequency of less than once a day. In additional exemplary embodiments, the antibiotic is administered once every two or three days or less, or every 2-8 days. In yet additional exemplary embodiments the antibiotic is administered once a week.

In some embodiments, the administered composition comprises a derivative of the antibiotic which is substantially devoid of antibacterial activity. In some exemplary embodiments, steroisomers of the compounds lacking antibacterial activity are used. The derivatives encompassed by the present invention include those that are capable of enhancing T cell activity.

The ability of a compound to enhance T cell activity may be determined using various in vitro and in vivo assays known in the art, for example, proliferation, cytokine secretion and the like.

In alternative or additional embodiments, the administered composition comprises a complex or conjugate of the beta-lactam antibiotic which is substantially devoid of antibacterial activity. In some embodiments, the antibiotic is conjugated to a protein. In some embodiments the protein is albumin.

In some embodiments, the administered composition comprises a beta-lactam compound devoid of direct anti-bacterial activity, or a salt thereof, selected from the group consisting of clavulanic acid, 6-APA and tazobactam. Each possibility represents a separate embodiment of the invention.

In some embodiments, the beta-lactam compound (either an antibiotic or a compound lacking antibacterial activity) is conjugated to albumin. According to these embodiments, the method comprises administering a pharmaceutical composition comprising as an active ingredient a conjugate of albumin and a beta-lactam compound capable of enhancing T cell activity, wherein the beta-lactam compound is selected from the group consisting of cefuroxime, a penicillin, ceftriaxone, clavulanic acid, 6-APA and tazobactam. Each possibility represents separate embodiment of the invention.

In some typical embodiments, the albumin is human serum albumin.

As noted above, the conjugation to albumin prolongs the half-life of the beta-lactam compound. Thus, a composition comprising an albumin-beta-lactam conjugate may be administered, for example, only once a week or less, for example every 10 days or less. In some exemplary embodiments, the conjugate is administered once every 4-14 days. Each subrange is within the scope of the present invention.

In some embodiments, the beta-lactam compound conjugated to the albumin is an antibiotic selected from the group consisting of cefuroxime, a penicillin, ceftriaxone. Each possibility represents separate embodiment of the invention. In some embodiments, the albumin-antibiotic conjugate is substantially devoid of anti-bacterial activity.

In some embodiments, the penicillin is selected from benzylpenicillin and phenoxymethylpenicillin. In some specific embodiments, the penicillin is benzylpenicillin.

In some embodiments, the beta-lactam compound conjugated to the albumin is a beta-lactam compound devoid of direct anti-bacterial activity, selected from the group consisting of clavulanic acid, 6-APA and tazobactam. Each possibility represents separate embodiment of the invention.

The method of the present invention may be applicable for a wide range of cancer types, including but not limited to, carcinomas (for example, respiratory system carcinomas, gastrointestinal system carcinomas, breast carcinomas, endocrine system carcinomas and melanomas), sarcomas (for example, bone or cartilage sarcomas), leukemias (for example, acute or chronic myelogenous leukemia, and acute or chronic lymphocytic leukemia), myelomas (for example, multiple myeloma) and lymphomas (for example, Hodgkin's and non-Hodgkin's lymphoma). Each possibility represents a separate embodiment of the invention. In a particular embodiment, the cancer is a T cell lymphoma. In some embodiments, the method is applied for the treatment of solid tumors. In some embodiments, the cancer type is other than prostate cancer.

As used herein, the term "treatment", when referring to cancer, encompasses inhibition of tumor growth or even tumor shrinkage. The term may also encompass prolongation of life. The beta-lactam compounds are administered in an amount which is effective to induce the anti-tumor effects.

In some embodiments, the subject is human. In other embodiments, the subject is a non-human mammal.

In some embodiments, a plurality of beta-lactam compounds are administered to the subject (e.g. penicillin and clavulanic acid).

In some embodiments, the beta-lactam compounds are administered in combination with another therapeutic agent, for example, an anti-cancer agent. "Therapeutic agents" that may be combined with the beta-lactam compounds of the present invention include active anti-tumor compounds as well as therapeutic methods such as radiation or surgery.

The method of the present invention may be combined with additional treatment or treatments.

According to another aspect, the present invention provides a pharmaceutical composition comprising a beta-lactam selected from the group consisting of cefuroxime, a penicillin, ceftriaxone, clavulanic acid, 6-APA and tazobactam, for use in enhancing a T cell mediated immune response in a subject. Each possibility represents separate embodiment of the invention.

In some embodiments, the composition further comprises a pharmaceutically acceptable diluent, solvent, excipient or carrier.

According to another aspect, the present invention provides a method for enhancing anti-tumor immune response in a subject, the method comprising administering to the subject a pharmaceutical composition comprising a beta-lactam compound selected from the group consisting of cefuroxime, penicillin, ceftriaxone, clavulanic acid, 6-APA and tazobactam. Each possibility represents separate embodiment of the invention.

In some embodiments, the immune response is T-cell mediated.

The enhancement of T cell activity as described herein may be performed ex vivo/in vitro. For example, T cells may be collected from a patient in need and subjected to mitogen stimulation in the presence of beta lactams (or a beta-lactam modified albumin). The stimulated T cells may then be re-infused to the patient. The ex-vivo exposure of patient's T cells to a beta-lactam compound as described herein may be used, for example, as a method of enhancing their anti-tumor effects.

Thus, according to a further aspect, the present invention provides a method for enhancing a T-cell-mediated immune response in a subject, the method comprising: (i) incubating T cells collected from the subject with a beta-lactam compound selected from the group consisting of cefuroxime, a penicillin, ceftriaxone, clavulanic acid, 6-APA and tazobactam; and (ii) re-infusing said T cells to said subject.

In some embodiments, the T cells are activated by a mitogen prior to re-infusion to the subject. Examples of suitable mitogens include phytohemagglutinin (PHA), or phorbol myristate acetate (PMA) in combination with ionomycin, or anti-CD3 antibodies. Mitogen stimulation of the T cells may be performed before incubation with the beta lactam compound, simultaneously or after incubation and before administration. Each possibility represents a separate embodiment of the invention. In some embodiments, the T cells are activated to up-regulate or enhance MHC class II expression.

In other embodiments, the T cells undergo antigen-specific activation prior to re-infusion to the subject. For example, the T cells may be activated by antigen-presenting cells (APC) presenting antigens specific to the tumor of the treated subject.

In some embodiments, the concentration of beta-lactam compound which is incubated with the T cells ranges from about 15-100 µg/ml, for example from about 15-60 µg/ml, from about 20-75 µg/ml, from about 20-65 µg/ml, from about 25-55 µg/ml. Each possibility represents a separate embodiment of the invention.

In some embodiments, the time of incubation of the beta-lactam compound with the T cells prior to administration to the subject ranges from 2-5 days, or from 1-4 days. Each possibility represents a separate embodiment of the invention. In some particular embodiments, the time of incubation is 3 days.

In other embodiments, the time of incubation of the beta-lactam compound with the T cells prior to administration to the subject ranges from about 1-3 hours, from about 1.5-2.5 hours. Each possibility represents a separate embodiment of the invention. In some particular embodiments, the time of incubation is 2 hours.

In some embodiments, the number of T cells that are re-infused to the patient ranges from about $10^6$-$10^8$, for example, about $10^7$ cells. Each possibility represents a separate embodiment of the invention.

In some embodiments, the method is utilized for enhancing anti-tumor immune response in a subject. According to these embodiments, the method is utilized for the treatment of cancer.

In other embodiments, the method is utilized for the treatment of viral infections.

According to yet another aspect, the present invention provides a method for ex-vivo enhancement of anti-tumor activity of T cells, the method comprising incubating the T cells with a beta-lactam compound selected from the group consisting of cefuroxime, penicillin, ceftriaxone, clavulanic acid, 6-APA and tazobactam.

In some embodiments, the method further comprises mitogen activation of the T cells. In other embodiments, the method further comprises antigen-specific activation of the T cells. For example, the T cells may be activated by antigens specific to a tumor of a certain subject.

These and further aspects and features of the present invention will become apparent from the figures, detailed description, examples and claims which follow.

DETAILED DESCRIPTION OF THE INVENTION

Figure 1A:
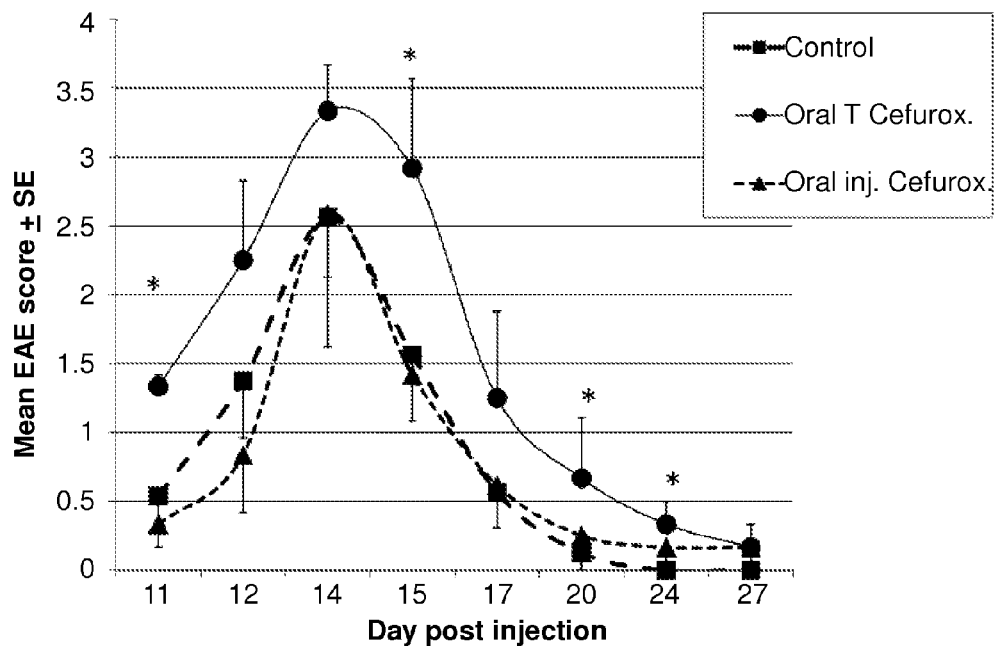
FIG. 1. Effects of beta-lactam antibiotics on experimental autoimmune diseases. A) Oral cefuroxime increases the severity of actively induced EAE. Asterisks indicate significant ($p<0.05$) changes between cefuroxime and control groups. B) Exacerbation of adjuvant-induced arthritis by cefuroxime treatment. C) Cefuroxime enhances the pathogenicity of the BP10 line. D) Inhibition of type I diabetes in NOD mice by ampicillin treatment.

The present invention is directed to the use of a specific group of beta-lactam compounds, either free or albumin-bound, in enhancing T cell mediated immune response, particularly tumor rejection.

The present invention is based in part on the unexpected finding that several commonly used beta-lactam antibiotics, as well as beta-lactam compounds devoid of antibacterial activity, promote tumor rejection in vivo. The present invention is further based on the following findings that bear important clinical and fundamental implications:
1. Certain beta-lactam compounds, including several antibiotics in common use, can act as modulators of T-cell behavior;
2. Different beta-lactam molecules can up-regulate pro-inflammatory T-cell phenotypes; and
3. The immune modulation appears to be mediated by interaction of the beta-lactam molecule with albumin produced by the T cells.

Albumin is widely known to be a blood protein produced by the liver and active in maintaining osmotic pressure in the vascular system and as a carrier for a variety of body molecules and drugs. Nevertheless, as exemplified hereinbelow, albumin expression was detected in several tissues and cells such as mesenchymal stem cells, dendritic cells, Jurkat, MOLT4, FAO and CEM lines. "Ectopic" albumin expression was previously described in healing bone, skin, granulosa cells, kidney and pancreas and mammary glands. Moreover, albumin was described to affect several biological processes: secretion of TGFβ1 by kidney tubular cells, and prevention of apoptosis in neuroblastoma cells, neuronal cells and CLL lymphocytes. In endothelial cells, albumin was found to activate the TGFβ receptor II and affect the phosphorylation and nuclear translocation of SMAD proteins. Other studies have found albumin to interact with DNA, transfer RNA and tumor associated peptides and proteins. Many pharmacological studies of albumin have identified the two major binding pockets of the molecule with specific endogenous and exogenous ligand-binding specific sites. There are earlier reports that penicillin binds covalently to albumin, and such binding affects the properties of albumin. However, albumin was not expected to be produced by immune cells or to acquire immune functions following an interaction with beta-lactams.

As further exemplified hereinbelow, albumin modified by beta-lactam antibiotics is taken up by T cells, and the modified albumin affects T-cell gene expression and behavioral phenotype. The chemical modification of bovine serum albumin by n-acetylglucosamine was previously described as a signal for nuclear translocation. Indeed, proteomic studies have identified albumin within nuclei. Interestingly, six of the genes that were modified by beta-lactam treatment of human CD4 T cells were situated in the TGFβ pathway (Table 1 hereinbelow), similar to the documented effect of albumin on endothelial cells. The modification of TGFβ-related genes is likely to be important, as recent work implicates TGFβ signaling at the crossroads of T cell differentiation into both Th17 effector cells and Treg cells. As the half-life of penicillin-modified albumin is prolonged to 7 days compared to the half-life of free penicillin of 42 minutes, the biological effects of modified albumin are likely to be prolonged.

In vitro culture of many cellular systems, including T cells, B cells and dendritic cells, is dependent upon addition of serum (such as autologous serum or fetal calf serum) or components derived therefrom. Mesenchymal stem cells and the PC12 pheochromocytoma cell line are also dependent on serum for growth in culture, and BSA was found to affect gene expression and cardiomyocyte differentiation in human embryonic stem cells. Human T cell growth media that are serum-free (AIM-V, Invitrogen) contain human albumin; similarly, growth of human embryonic stem cells without serum necessitates albumin. Thus, it may be concluded that the presence of serum components and specifically albumin is important for cell survival and proliferation in many cell systems.

In the medical literature, there are many publications linking exacerbation of a Th1 type human autoimmune disease, e.g. multiple sclerosis, to infections. These infections were of suspected viral origin of the respiratory tract or bacterial origin of the sinuses or urinary tract. While the suggested mechanism implicated the Th1 cytokines released during the infection as stimulatory to the auto-reactive T cells, the data presented herein point to the use of penicillins during such infections as potential exacerbating factors in this setting. Indeed, ampicillin-specific rashes have been noted to occur during viral infections such as infectious mononucleosis, and these rashes cannot always be attributed to penicillin hypersensitivity.

The data presented herein therefore documents novel and significant effects of beta-lactam compounds, including antibiotics and non-antibacterial compounds, on T cell functions. Without wishing to be bound by any particular theory or mechanism of action, the effect may involve chemical modification of albumin, leading to widespread changes in cellular genes leading to a change in T cell behavior.

According to one aspect, the present invention provides a method for enhancing T cell mediated immune response in a subject. In some embodiments, the subject has cancer. In other embodiments, the subject has a viral infection.

In some embodiments, a method for treating cancer is provided. In other embodiments, a method for treating a viral infection is provided.

In some embodiments, the methods of the present invention comprise administering to the subject a pharmaceutical composition comprising a beta-lactam compound or a salt thereof capable of enhancing T cell activity, wherein the beta-lactam compound is selected from the group consisting of cefuroxime, a penicillin, ceftriaxone, clavulanic acid, 6-APA and tazobactam. Each possibility represents separate embodiment of the invention.

According to another aspect, the present invention provides a pharmaceutical composition comprising as an active ingredient a beta-lactam compound selected from the group consisting of cefuroxime, a penicillin, ceftriaxone, clavulanic acid, 6-APA and tazobactam, for use in enhancing T cell mediated immune responses. Each possibility represents separate embodiment of the invention.

In some embodiments, the composition further comprises a pharmaceutically acceptable diluent, solvent, excipient or carrier.

According to another aspect, the present invention provides a method for enhancing an anti-tumor immune response in a subject, the method comprising administering to the subject a pharmaceutical composition comprising a beta-lactam compound selected from the group consisting of cefuroxime, penicillin, ceftriaxone, clavulanic acid, 6-APA and tazobactam, for use in the treatment of cancer. Each possibility represents separate embodiment of the invention.

In some embodiments, the immune response is T-cell mediated.

According to yet another aspect, the present invention provides a method for enhancing anti-tumor T-cell response, the method comprising exposing the T cells to a beta-lactam compound selected from the group consisting of cefuroxime, penicillin, ceftriaxone, clavulanic acid, 6-APA and tazobactam. Each possibility represents separate embodiment of the invention.

According to a further aspect, the present invention provides a method for enhancing T-cell-mediated immune response in a subject, the method comprising: infusing to the subject T cells obtained from said subject and incubated ex vivo with a beta-lactam compound selected from the group consisting of cefuroxime, a penicillin, ceftriaxone, clavulanic acid, 6-APA and tazobactam. Each possibility represents separate embodiment of the invention.

In some embodiments, the method comprises: (i) collecting T cells from the subject; (ii) incubating the T cells with at least one of the beta-lactam compounds noted above; and (iii) re-infusing said T cells to said subject.

In some embodiments, collecting T cells from the subject comprises collecting a sample of peripheral blood from the subject, and purifying the T cells from the blood sample. Methods for purifying T cells are known in the art, an exemplary procedure is described in the Examples section below. T cells may also be collected by lymphopheresis, as known in the art. In some embodiments, the collected T cells are subjected to further separation processes, for example, to isolate $CD4^+$ T cells.

In some embodiments, tumor-infiltrating lymphocytes (T cells) are isolated from a surgically removed tumor; the anti-tumor antigen lymphocytes are activated by incubating them with the tumor cells in vitro in the presence of a beta lactam as disclosed herein for e.g. 2 hours or for 3-6 days, and the treated T cells are infused back into the subject.

In additional embodiments, peripheral blood mononuclear cells are collected from the subject and incubated with tumor cells or tumor antigens in vitro in the presence of a beta lactam to sensitize the subject's immune cells against tumor antigens—e.g. for 3-6 days. The treated cells are then infused back into the subject.

In some embodiments, the method is utilized for enhancing anti-tumor immune response in a subject. According to these embodiments, the method is utilized for the treatment of cancer.

In other embodiments, the method is utilized for the treatment of viral infections.

In some embodiments, the T cells are activated by a mitogen such as PHA, PMA-ionomycin or anti-CD3 antibodies, prior to re-infusion to the subject. An exemplary procedure for activating T cells is described in the Examples section below. Mitogen stimulation of the T cells may be performed before incubation with the beta lactam compound, simultaneously or after incubation and before administration. Each possibility represents a separate embodiment of the invention. In some embodiments, the T cells are activated to upregulate or enhance MHC class II expression.

In some embodiments, the T cells undergo antigen-specific activation prior to re-infusion to the subject. For example, the T cells may be activated by antigens specific to the tumor of the treated subject.

The concentration of beta-lactam compound which is incubated with the T cells may range from about 15-60 μg/ml, for example, about from 20-55 μg/ml, from about 25-50 μg/ml. Each possibility represents a separate embodiment of the invention.

As used herein, the term "about", when referring to a measurable value such as an amount, a temporal duration, and the like, is meant to encompass variations of .+−0.10%, more preferably .+−0.5%, even more preferably .+−0.1%, and still more preferably .+−.0.1% from the specified value, as such variations are appropriate to perform the disclosed methods.

The time of incubation of the beta-lactam compound with the T cells prior to administration to the subject may range from about 2-5 days, from about 1-4 days. For example, the time of incubation may be about 3 days. Each possibility represents a separate embodiment of the invention.

Alternatively, the time of incubation of the beta-lactam compound with the T cells prior to administration to the subject may range from about 1-3 hours, from about 1.5-2.5 hours. For example, the time of incubation may be about 2 hours. Each possibility represents a separate embodiment of the invention.

The number of T cells that are re-infused to the patient may range from about $10^6$-$10^8$, for example, about $10^7$ cells. Each possibility represents a separate embodiment of the invention.

According to yet another aspect, the present invention provides a method for ex-vivo enhancement of anti-tumor activity of T cells, the method comprising incubating the T cells with a beta-lactam compound selected from the group consisting of cefuroxime, penicillin, ceftriaxone, clavulanic acid, 6-APA and tazobactam. Each possibility represents a separate embodiment of the invention.

T cells in need of enhancement of their anti-tumor activity may include tumor infiltrating T lymphocytes (known as TILs). Thus, in some embodiments, the in-vitro/ex-vivo methods of the present invention are applied to tumor-infiltrating T cells isolated from a subject's tumor.

Collection of samples from a tumor, as well as isolation of tumor infiltrating T cells may be performed by methods known in the art.

In some embodiments, the methods of the present invention are utilized for the treatment of viral infections. Suitable viral infections that may be treated include, but are not limited to, HIV (human immunodeficiency virus), CMV (cytomegalovirus), EBV (Epstein-Barr virus), herpes and influenza—including avian and swine. Each possibility represents a separate embodiment of the invention. In some embodiments, the viral infections include a chronic viral infection. In some embodiments, the viral infections include a viral infection in an immune compromised host—e.g., allograft recipient; subjects on steroids. In other embodiments, the treated subject is not immune-compromised.

Application of the methods and compositions of the present invention may also be useful for the treatment of bacterial or parasitic infections whose eradication involves T cell activation. In some embodiments, these infections are associated with or caused by bacteria not sensitive to beta-lactam antibiotics. In alternative or additional embodiments, the treated subject is not otherwise amenable to treatment with beta-lactam antibiotics.

According to another aspect, the present invention provides a pharmaceutical composition comprising a beta-lactam compound capable of enhancing T cell activity, wherein the beta-lactam compound is selected from the group consisting of cefuroxime, penicillin, ceftriaxone, clavulanic acid, 6-APA and tazobactam, for use in the treatment of viral infections. Each possibility represents separate embodiment of the invention.

In some embodiments, the beta-lactam compound used in the compositions and methods of the present invention is an antibiotic or a salt thereof, selected from the group consisting of cefuroxime, penicillin, ceftriaxone. Each possibility represents separate embodiment of the invention. In some embodiments, the penicillin is selected from benzylpenicillin and phenoxymethylpenicillin.

In some embodiments, the beta-lactam compound used in the compositions and methods of the present invention is a beta-lactam compound devoid of direct anti-bacterial activity, or a salt thereof, selected from the group consisting of clavulanic acid, 6-APA and tazobactam. Each possibility represents separate embodiment of the invention. These compounds do not have direct antibacterial activity—they do not kill bacteria directly in the absence of other compounds.

The beta-lactam compounds or salts thereof utilized according to embodiments of the present invention are commercially available, and may also be synthesized using methods known in the art. Cefuroxime may be identified by CAS registry number 55268-75-2, benzylpenicillin (penicillin G) may be identified by CAS registry number 61-33-6, phenoxymethylpenicillin (penicillin V) may be identified by CAS registry number 87-08-1, ceftriaxone may be identified by CAS registry number 73384-59-5, clavulanic acid may be identified by CAS registry number 58001-44-8, 6-aminopenicillanic acid may be identified by CAS registry number 551-16-6 and tazobactam may be identified by CAS registry number 89786-04-9. Information about the chemistry and synthesis of beta-lactam compounds can be found, for example, in Bruggink (ed.) Synthesis of β-lactam antibiotics: chemistry, biocatalysis & process integration, 2001, Springer; and Page (ed.) The Chemistry of [beta]-lactams, 1992, Blackie Academic & Professional.

In some embodiments, pharmaceutically acceptable salts of the beta-lactam compounds are used. Non-limiting examples of suitable salts include potassium and sodium salts. Pharmaceutically acceptable salts of the compounds described herein are salts that do not substantially contribute to the toxicity of the compound. Such salts can be formed by well known procedures.

In some embodiments, the beta-lactam compound (either an antibiotic or a compound lacking antibacterial activity) is conjugated to, or complexed with, albumin. According to these embodiments, the methods of the present invention comprise administering a pharmaceutical composition comprising as an active ingredient a conjugate of albumin and a beta-lactam compound, wherein the beta-lactam compound is selected from the group consisting of cefuroxime, penicillin, ceftriaxone, clavulanic acid, 6-APA and tazobactam. Each possibility represents separate embodiment of the invention.

In some typical embodiments, the albumin is human serum albumin.

Advantageously, the conjugation to albumin prolongs the half-life of the beta-lactam compound. Thus, the treatment regime with a composition comprising an albumin-beta-lactam conjugate may include fewer administrations per a given period of time compared to that of a free beta-lactam compound.

In some embodiments, the beta-lactam compound conjugated to the albumin is an antibiotic selected from the group consisting of cefuroxime, a penicillin and ceftriaxone. Each possibility represents separate embodiment of the invention.

In some embodiments, the albumin-antibiotic conjugate is substantially devoid of anti-bacterial activity.

As used herein, "substantially devoid of anti-bacterial activity" indicates no or only negligible activity, of no clinical significance.

In some embodiments, the penicillin is benzylpenicillin. In other embodiments, the penicillin is phenoxymethylpenicillin.

In some embodiments, the beta-lactam compound conjugated to the albumin is a beta-lactam compound devoid of direct anti-bacterial activity, selected from the group consisting of clavulanic acid, 6-APA and tazobactam. Each possibility represents separate embodiment of the invention.

Albumin, including human serum albumin, is commercially available, and may also be synthesized using, e.g., recombinant methods known in the art. In order to prepare an albumin-beta-lactam conjugate, the two components may be mixed and incubated. For example, the two components may be mixed at an alkaline pH, which favors a reaction between the beta-lactam compound and amino groups in lysine residues of the protein.

In some embodiments, the beta-lactam compounds used in the methods and compositions of the present invention are beta-lactam antibiotics. It was surprisingly found that the beta-lactam antibiotics according to embodiments of the present invention exert their anti-tumor activity even when administered in an amount which is less than that required for producing a clinically effective anti-bacterial effect, namely, a sub-antibacterial amount. In some embodiments, a sub-antibacterial dose of the antibiotic is administered. According to these embodiments, the pharmaceutical composition comprises a sub-antibacterial dose of the beta-lactam antibiotic. The lower dose of the antibiotic has substantially no antibacterial activity and does not significantly prevent the growth of bacteria. In some embodiments, the composition comprises about 90% or less, about 70% or less, about 50% or less of the known antibacterial amount. Each possibility represents a separate embodiment of the invention.

For example, penicillin V for oral administration is available, inter alia, as capsules containing 250 mg of the antibiotic. In some exemplary embodiments, a pharmaceutical composition for oral administration in human may comprise about 225 mg penicillin V or less, about 175 mg or less, about 125 mg or less, about 75 mg or less, about 25 mg or less. Each possibility represents a separate embodiment of the invention.

For beta-lactam compounds that do not have an anti-bacterial activity, suitable doses for humans may range, for example from about 250 mg to about 2 grams, or less than 250 mg, for example between about 225-175 mg, between 175-125 mg, or less than 125 mg. Each possibility represents a separate embodiment of the invention.

In alternative or additional embodiments, the antibiotic is administered in a treatment regime that is different from the typical anti-bacterial treatment regime known for the antibiotic, such that substantially no antibacterial effect is provided. In some embodiments, the antibiotic is administered fewer times per day compared to the antibacterial treatment regime. For example, the antibiotic may be administered once every two or three days or less. Each possibility represents a separate embodiment of the invention. In additional exemplary embodiments the antibiotic is administered once a week or less.

In some embodiments, a substantially non-antibacterial derivative of the antibiotic is used.

In some exemplary embodiments, stereoisomers of the compounds are used. The derivatives encompassed by the present invention include those that are capable of enhancing T cell activity.

In some embodiments, the derivatives are other than N-thiolated beta-lactam compounds. In additional embodiments, the derivatives are other than 4-alkylidene-betalactams. In yet additional embodiments, the derivatives are other than beta-lactam compounds with polyaromatic substituents. In yet additional embodiments, the derivatives are other than modified penicillin sulfoxide esters or penicillin sulfone esters.

The ability of a compound to enhance T cell activity may be determined, for example, using an in vivo assay testing the effect of a given compound on the severity of adoptive (passive) EAE, namely, EAE which is induced by the injection of activated encephalitogenic T cell line to the model animal. In order to test a compound, the encephalitogenic T cells are activated in the presence of the compound prior to injection. An exemplary procedure is described in the Examples section hereinbelow. Compounds whose incubation with the encephalitogenic T cells prior to injection results in an increased disease severity compared to a disease induced by T cells that were not incubated with the test compound, may be suitable for use according to embodiments of the present invention.

The ability of a compound to enhance T cells activity may also be determined using an in vitro assay testing the effect of a given compound on expression of immune-related genes in T cells, for example using the gene array described in the Examples section hereinbelow. In order to test a compound, purified T cells are stimulated in the presence of the compound and the effect on gene expression is then determined. An exemplary procedure is described hereinbelow. Compounds that down-regulate the expression of the genes listed in Table 1 hereinbelow, or a significant portion thereof, may be suitable for use according to embodiments of the present invention. Alternatively, compounds that down-regulate the expression of the following genes may also be suitable: CCR4, ACVR2, JAK1, STAT4, TLR2 and NFKBIE.

In some embodiments, a pro-drug of the beta-lactam antibiotic which is substantially devoid of antibacterial activity is used. In some embodiments, the antibiotic is conjugated to, or complexed with, a protein, for example, albumin.

Various assays are known in the art for testing antibacterial activity of a given compound, e.g. zone of inhibition screening test or agar disc diffusion method. Such assays may be applied to the derivatives and/or conjugates and/or pro-drugs according to embodiments of the present invention to determine their antibacterial activity, if any.

Cancer types that be treated according to embodiments of the present invention include, but are not limited to, carcinomas (for example, respiratory system carcinomas, gastrointestinal system carcinomas, breast carcinomas, endocrine system carcinomas and melanomas), sarcomas (for example, bone or cartilage sarcomas), leukemias (for example, acute or chronic myelogenous leukemia, and acute or chronic lymphocytic leukemia), myelomas (for example, multiple myeloma) and lymphomas (for example, Hodgkin's and non-Hodgkin's lymphoma). In a particular embodiment, the cancer is a T cell lymphoma. Each possibility represents a separate embodiment of the invention. In some embodiments, solid tumors are treated. In some embodiments, cancer types where tumor rejection is immune-mediated are treated. A non-limiting example of such cancer type includes melanoma. In some embodiments, the cancer type is other than prostate cancer.

In some embodiments, treatment comprises inhibition of tumor growth or even tumor shrinkage. In some embodiments, treatment comprises prolongation of life.

In some embodiments, the subject is human. In some embodiments, a subject not having a human blood bacterium in the blood is treated. In other embodiments, the subject is a non-human mammal.

In some embodiments, a plurality of beta-lactam compounds are administered to the subject (a non-limiting example includes penicillin and clavulanic acid).

In some embodiments, the beta-lactam compounds are administered in combination with another therapeutic agent, for example, an anti-cancer agent. As used herein, "in combination" includes both sequential and concurrent administration of the different active agents.

In some embodiments, the methods of the present invention are combined with additional treatment or treatments.

Pharmaceutical compositions of the present invention are preparations of one or more active ingredients with other chemical components such as physiologically acceptable carriers and excipients. The purpose of a pharmaceutical composition is to facilitate administration of a compound to an organism.

As used herein, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered active agent.

As used herein, the term "excipient" refers to an inert substance added to a pharmaceutical composition to further facilitate administration of an active ingredient. Non-limiting examples of excipients include calcium carbonate, calcium phosphate, various sugars and types of starch, cellulose derivatives, gelatin, vegetable oils, and polyethylene glycols. Techniques for formulation and administration of drugs may be found in "Remington's Pharmaceutical Sciences", Mack Publishing Co., Easton, Pa., (Remington: The Science and Practice of Pharmacy, Gennaro, A., Lippincott, Williams & Wilkins, Philadelphia, Pa., 20th ed, 2000). Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are particularly suitable for administration systemically. Systemic administration includes all enteral and parenteral routes. Non-limiting examples of suitable administration routes include oral, rectal, transmucosal such as transnasal and buccal, intravenous, intramuscular, transdermal, subcutaneous, intradermal, intravesicular and inhalation routes. The appropriate route of administration and formulation may be determined, in some embodiments, according to the properties of the active ingredient. For example, where the active ingredient is a conjugate of a beta-lactam compound and a protein, for example a beta-lactam-albumin conjugate, the proper formulation may be for parenteral administration, e.g. injection.

For injection, the active ingredients of the pharmaceutical composition may be formulated in aqueous solutions, preferably in physiologically compatible buffers such as Hank's solution, Ringer's solution, or physiological salt buffer. Pharmaceutical compositions for potential administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carboxymethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added. Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Alternative embodiments include depots providing sustained release or prolonged duration of activity of the active ingredient in the subject, as are well known in the art.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein.

The present invention further provides kits. In some embodiments, a kit is provided, for enhancing a T cell mediated immune response in a subject.

In some embodiments, the kit comprises a composition comprising at least one of the beta-lactam compounds noted above or salts or derivatives thereof, and may also include instructions for administering said composition to a subject in need thereof. Such instructions may include, for example, a dosing regimen.

In some embodiments, the kit comprises means for administering the composition or compositions. For example, for injection administration, the kit may include a syringe.

In some embodiments, a kit for in vitro/ex vivo enhancement of T cell mediated immune responses is provided. In some embodiments, the kit comprises one or more of the beta-lactam compounds noted above or salts or derivatives thereof. Such kit may further include at least one of means for collecting a blood sample from a subject, means for isolating T cells from a blood sample, and means for re-infusing T cells treated with the beta-lactam compound back to the subject. For example, the kit may include syringes, tubes, infusion bags, collection bags. The kit may further include instructions for performing the ex-vivo procedure.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods

Animals:

Inbred female Lewis rats and NOD (non-obese diabetic) mice were supplied by the animal breeding center of the Weizmann Institute of Science, Israel, under the supervision of Harlan Laboratories and were used at 2-3 months of age. Experiments were approved by the Institutional Animal Care and Use Committee. Human peripheral blood lymphocytes from healthy donors were obtained from the blood bank of Sheba Medical Center, Tel Hashomer, Israel.

Reagents, Antigens and Antibodies:

*Mycobacterium tuberculosis* H37Ra was purchased from Difco (Detroit, Mich.). Guinea-pig myelin basic protein and Concanavalin A (ConA) were purchased from Sigma (Rehovot, Israel). Antibiotics were purchased from a local pharmacy. Anti-human CD3 (OKT3, eBioscience, San Diego, Calif.) was used to coat 24 well plates at 2 μg/ml in PBS. Rabbit polyclonal anti-human serum albumin was purchased from SIGMA (Rehovot, Israel, Catalogue number A0433). Mouse monoclonal anti-penicillin (Pen 9) was from AbD-Serotec (Oxford UK). Captavidin was from Invitrogen, (Carlsbad, Calif. USA) and Sulfo-NHS-LC Biotin was from Pierce (Rockford, Ill., USA).

Realtime PCR primers for rat albumin were: forward primer CCCGATTACTCCGTGT (SEQ ID NO.: 1); reverse primer: TGGCGTTTTGGAATCCATA (SEQ ID NO.: 2). Human primers for albumin were forward ATGCGCTATT-AGTTCGTTAC (SEQ ID NO.: 3); reverse primer CATG-GTCGCCTGTTCA (SEQ ID NO.: 4).

Radioactive $^3$[H] benzylpenicillin was purchased from Amersham (Buckinghamshire, UK; 250 μCi, 1 mCi/ml). Human albumin was from Calbiochem (Merck Darmstadt, Germany).

T-Cell Lines:

Antigen-specific T-cell lines were established from lymph node cells that had been stimulated with myelin basic protein (MBP; 10 µg/ml) for 3 days in stimulation medium as described below. Following stimulation, the T-cell blasts were isolated on Lympho-prep (Nycomed Pharma, Oslo, Norway) and seeded in propagation medium. Propagation medium was identical to stimulation medium without autologous serum, but supplemented with fetal calf serum 10% and T-cell growth factors from the supernatant of Con A stimulated spleen cells 10% (Mor et al. (1990) *J Clin Invest*, 85, 1594-1598). Animals were injected intra-peritoneally with $10^7$ MBP-stimulated T cells, following 6-8 cycles of in vitro stimulations. It is known that MBP-reactive lines undergo a reduction in pathogenicity after 6 or more in vitro stimulations. In some experiments the BP10 line was stimulated with phorbol myristate acetate (PMA; 50 ng/ml) and ionomycin (500 ng/ml) for 3 days in stimulation medium, without antigen-presenting cells.

Induction of EAE:

Active EAE was induced by subcutaneous injection of 25 µg guinea-pig MBP (GpMBP) in complete Freund's adjuvant (CFA). CFA was prepared by adding 4 mg/ml *Mycobacterium tuberculosis* H37Ra (Difco, Mich.) to incomplete Freund's adjuvant (IFA). Adoptive EAE was transferred by intra-peritoneal injection of guinea-pig MBP-activated cells of the BP10 line as described in Mor et al. (1993) *J Clin Invest*, 92, 2199-2206. Clinical EAE was observed 4-6 days following administration of T-cell line and 11-12 days following GpMBP/CFA injection. Clinical scoring was: +1, paralysis of tail; +1.5, paresis of posterior paws and ataxia; +2, paraplegia; +3, paralysis extending to thoracic spine; +4, a moribund state.

AA Induction and Assessment:

Heat-killed *Mycobacterium tuberculosis* (Mt) strain H37Ra (Difco) was finely ground using a pestle and mortar, and was suspended to a final concentration of 10 mg/ml in IFA. Test rats were injected at the base of the tail with a total of 100 µl of the Mt suspension. The day of AA induction was designated as day 0. Disease severity was assessed by direct observation of all four limbs in each animal. A relative score between 0 and 4 was assigned to each limb based on the degree of joint inflammation, redness, and deformity; thus, the maximum possible score for an individual animal was 16. The results are presented as the mean±SE of total score.

Radioactive Penicillin Binding Assay:

Tritium labeled benzylpenicillin was obtained from Amersham (Buckinghamshire, UK; 250 µCi, 1 mCi/ml). Human CD4 or CD8 T cells were stimulated in 24 well plates, $5 \times 10^6$ cells per ml, with PMA and Ionomycin for 72 hr in the presence of 10 or 20 µCi of labeled penicillin. Following stimulation, the cells were collected, lysed and separated by SDS PAGE. The gels were fixed, treated with 1M sodium salicylate, and dried. The dried gels were exposed to x-ray film (BioMax MS film) for 14 days, with intensifying screen (BioMax TranScreen, Eastman Kodak Co., New Haven Conn., USA), and were developed.

Human T Cells:

T cells were purified from the peripheral bloods of healthy human donors (Blood Bank, Sheba Medical center). The whole blood was incubated (20 min, 22° C.) with Rosette-Sep™ human T cell enrichment mixture (StemCell Technologies, Vancouver, Canada). The remaining unsedimented cells were then loaded onto lymphocyte separation medium (ICN Biomedicals, Irvine, Calif.), isolated by density centrifugation, and washed with PBS. The purified cells were 95% CD3$^+$ T cells. In a second round of purification, CD3$^+$ T cells were labeled for selection with a magnetically coupled mAb against CD4 (Miltenyi Biotec, Auburn, Calif.). The purified cells obtained (usually 97% CD4$^+$ T cells) were cultured in RPMI 1640 medium containing 10% heat-inactivated FCS.

Western Blot:

Rat tissues were ground with a tissue grinder in lysis buffer. The homogenate was centrifuged 14000 g for 15 min in 4° C. and the supernatant was used for western blotting. The protein concentration was determined using the Bio-Rad Dc protein assay (Bio-Rad laboratories, Hercules, Calif.). Following electrophoresis in SDS gel in a mini-gel apparatus (Bio-Rad), the gels were electro-transferred to nitrocellulose membranes (Schleicher and schuell, Dassel, Germany). The nitrocellulose membranes were washed with distilled water for 5 min, and then blocked for 60 min. using a blocking solution composed of 2% bovine serum albumin (Fraction V, Sigma, St. Louis Mo.), 2.5% milk powder (Bio-Rad), Tris (Sigma) pH 7.5 10 mM, NaCl 150 mM and 0.02% thimerosal (Sigma). After 3×10 min. washes in PBS/Tween 20 (PBS/T; 0.02%, Sigma), primary antibodies (1/1000) were incubated with the membranes in PBS/Tween for 60 min. Following another series of washes in PBS/T (3×10 min), the membranes were incubated with a secondary antibody (Peroxidase conjugated anti rabbit or anti mouse, IgG Jackson ImmunoResearch, West Grove, Calif.) at a 1/2500 dilution in 2% milk in PBS solution for 60 min. After another 3×10 min washes, the membranes were incubated with the ECL reagent (for 60 seconds) and exposed to X-ray film.

Immunoprecipitation:

For immunoprecipitation experiments, T cells were incubated with penicillin (50 µg/ml), for the times indicated and then lysed in lysis buffer. Lyzates were incubated with rabbit polyclonal antibody to human serum albumin (Sigma, 1 hr RT). Next, we incubated the mixture with Protein A sepharose for 1 hr, and after 3 washes in PBS the bound proteins were eluted with sample buffer by heating to 95° C. for 5 min and run in SDS gels. The 67 kD band was excised, digested with trypsin and subjected to mass spectrometry as described in Mor et al. (2005) *J Immunol*, 175, 3439-3445.

Gene-Array Experiments:

Human CD4 T cells were isolated as described, and incubated in 24 well plates (Nunc), $4 \times 10^6$ cells/ml with plate bound anti-human CD3 (OKT3) at 2 µg/ml. The stimulation was performed in RPMI medium supplemented with 0.1% BSA. After 2 hours of stimulation with or without cefuroxime (50 µg/ml) or ampicillin (50 µg/ml), cells were collected washed and suspended in TRI REAGENT (Molecular research center, Cincinnati, Ohio). RNA was extracted from samples and used to prepare probes for gene array in accord with the manufacturer's instructions (SuperArray Bioscience, Frederick, Md.). Adequate labeling of the probes was tested before hybridization. Three healthy donors were tested in stimulation with cefuroxime. The membranes were analyzed online with the Image Data Acquisition and Expression Analysis (SuperArray Bioscience).

Real-Time PCR Analysis:

To verify the results of the gene array, we synthesized real-time PCR primers (designed with the LightCycler probe design software (Roche)). Real-time PCR of 6 selected genes was performed using a LightCycler (Roche, Basel, Switzerland). RNA was reverse transcribed to cDNA from 1 µg of total RNA, which was then subjected to quantitative RT-PCR performed essentially according to the manufacturer's instructions. Specific primer pairs were used to amplify specific genes in the presence of 3 mM MgCl$_2$. PCR was performed in triplicate in a total volume of 20 µl of LightCycler HotStart DNA SYBR Green I mix (Roche) containing primer and 5 µl of cDNA. PCR amplification was preceded by incubation of the mixture for 10 min at 95° C., and the amplification step consisted of 45 cycles of denaturation, annealing, and extension. Denaturation was performed for 15 s at 95° C., annealing was performed in 60° C., and the extension was performed at 72° C. for 20 s, with fluorescence detection at 72° C. after each cycle. After the final cycle, melting point analyses of all samples were performed within the range of 62-95° C. with continuous fluorescence detection. A standard curve was generated from one sample in each run. Expression levels of β2-microglobulin (B2M) were used for sample normalization (β-actin levels were affected by cefuroxime treatment). The primer sequences were:

B2M sense TAGCTCTAGGAGGGCTG (SEQ ID NO.: 5) anti-sense ACCACAACCATGCCTTA (SEQ ID NO.: 6); ACVR2 sense ATCTCCGCGTAAGGAA (SEQ ID NO.: 7), anti-sense TGGGACTAACAATCGTG (SEQ ID NO.: 8); CCR4 sense TCCTAGAGACCCTGGTG (SEQ ID NO.: 9), anti-sense GGACTGCGTGTAAGATG (SEQ ID NO.: 10); JAK1 sense AGGAGTATTACACCGTCAAG (SEQ ID NO.: 11), anti-sense GGGTTGGGCCTATCAT (SEQ ID NO.: 12); STAT4 sense ACATCCTGCGAGACTAC (SEQ ID NO.: 13), anti-sense CACCGCATACACACTT (SEQ ID NO.: 14); TLR2 sense CTTCTGGAGCCCATTG (SEQ ID NO.: 15), anti-sense ACGGTACATCCACGTAG (SEQ ID NO.: 16); NFKBIE sense GACTTTGTGGTAGAGGCA (SEQ ID NO.: 17), anti-sense AAAACGTGGAGTCAGC (SEQ ID NO.: 18).

Results for each gene are presented as the relative expression level compared with B2M. Comparison between membranes was performed after normalization in accord with the manufacturer instructions.

Statistical Analysis:

The animal disease scores were compared using Mann-Whitney test.

Example 1

Figure 1B:
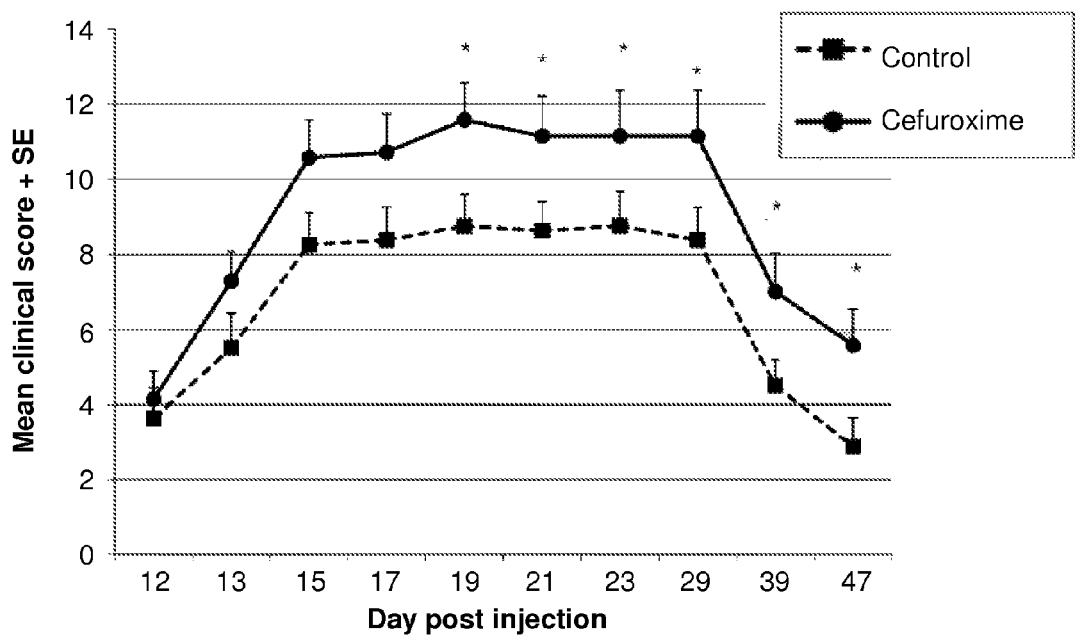

Enhancement of Actively Induced EAE and Adjuvant Arthritis by Cefuroxime Treatment To test the effects of antibiotics in vivo, active experimental autoimmune encephalomyelitis (EAE) was induced in rats as described above, and the injected rats (4 per group) were treated with oral cefuroxime axetil in the drinking water from day 7 postinduction ("Oral T Cefurox."). One 500 mg tablet was dissolved in 500 ml of drinking water. The daily dose was 50 mg/kg, in the range of therapeutic pediatric human doses. As a control, the intravenous cefuroxime sodium preparation, which is not absorbed into the circulation, was administered orally ("Oral inj. Cefurox."). A second control group was given water without antibiotics ("Control"). As can be seen in FIG. 1A, the rats that received oral cefuroxime developed significantly more severe EAE than the two control groups. To extend the results to another experimental autoimmune disease, Adjuvant Arthritis (AA), two groups of 8 rats each were injected with CFA. On day 12 post-injection the rats were divided into two groups with similar disease scores. One group was injected IP with cefuroxime 5 mg (25 mg/kg) on the days indicated in the graph presented in FIG. 1B, and the second group was non-injected and served as a control. The chosen treatment regime, once every 2 or 3 days, was different from the anti-bacterial dosing regime (3 daily injections), in order to differentiate the immuno-modulating effect from an anti-bacterial effect. As can be seen in FIG. 1B, the rats that had been injected with cefuroxime showed significantly more severe arthritis scores compared to the control group. Thus, the enhancing effects of cefuroxime were manifested in two experimental autoimmune diseases.

Example 2

Cefuroxime Treatment of Encephalitogenic T Cells Enhances Adoptive EAE

Figure 1C:
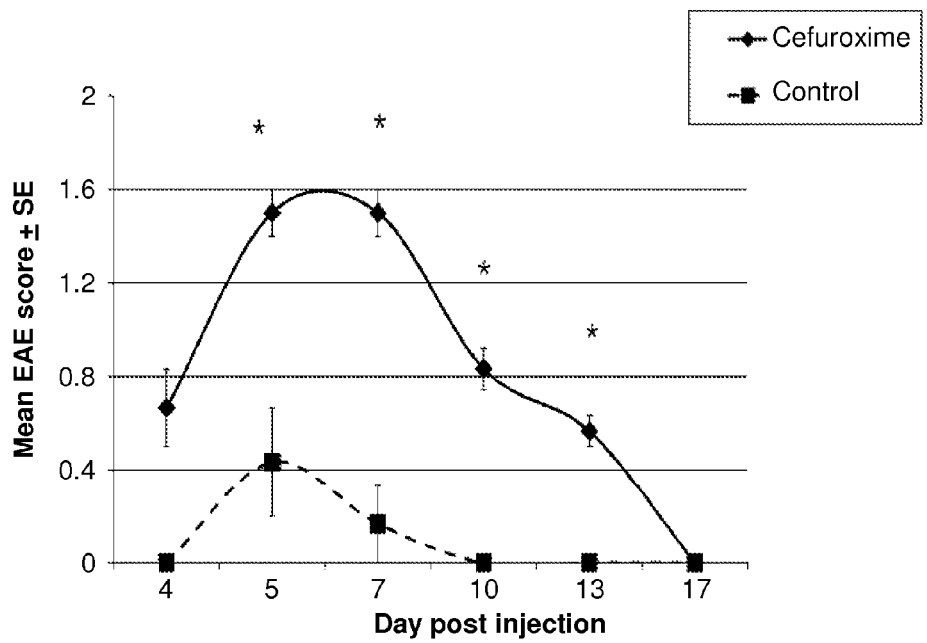

Treatment with cefuroxime in vivo could affect many different host agents involved in EAE or AA as well as influencing the rats' bacterial flora. To test whether the antibiotic might directly modify the behavior of effector T cells, an encephalitogenic T-cell line was stimulated in the presence or absence of cefuroxime in vitro. The weakly encephalitogenic BP10 line was used, and was stimulated for 3 days with MBP in the presence or absence of cefuroxime (50 µg/ml). The activated T cells were then washed to remove the antibiotic, the T cells were injected intra-peritoneally into naïve recipient rats ($10^7$ per rat), and EAE was scored. The BP10 line at later stimulations was used, when its pathogenic potential is reduced, allowing to detect both suppression and enhancement of disease. As can be seen in FIG. 1C, the presence of cefuroxime during T-cell activation markedly enhanced the manifestations of EAE in the recipient rats. A dose-response experiment showed that cefuroxime at 5 µg/ml was ineffective, but 25 µg/ml had an enhancing effect similar to that of 50 µg/ml. A similar enhancing effect was seen upon incubation of the BP10 line with 50 µg/ml of another beta-lactam antibiotic, penicillin. To rule out antigen presenting cells (APC) as the target of the beta-lactam antibiotic, the encephalitogenic BP10 line was stimulated without APC using PMA (50 ng/ml) and Ionomycin (500 ng/ml) in the presence or absence of cefuroxime. The EAE mediated by the T cells stimulated in the presence of cefuroxime was significantly more severe, indicating that the antibiotic directly affected the encephalitogenic T cells.

Example 3

Different Beta-Lactam Antibiotics Enhance EAE

Several beta-lactam antibiotics were tested for their effect on the adoptive transfer of EAE. The BP10 line was incubated with cefuroxime, ceftriaxone or ampicillin (at 50 µg/ml). Ceftriaxone enhanced EAE severity, as did cefuroxime, but ampicillin treatment did not increase the severity of EAE.

Example 4

Ampicillin Protects NOD Mice from Diabetes

Figure 1D:
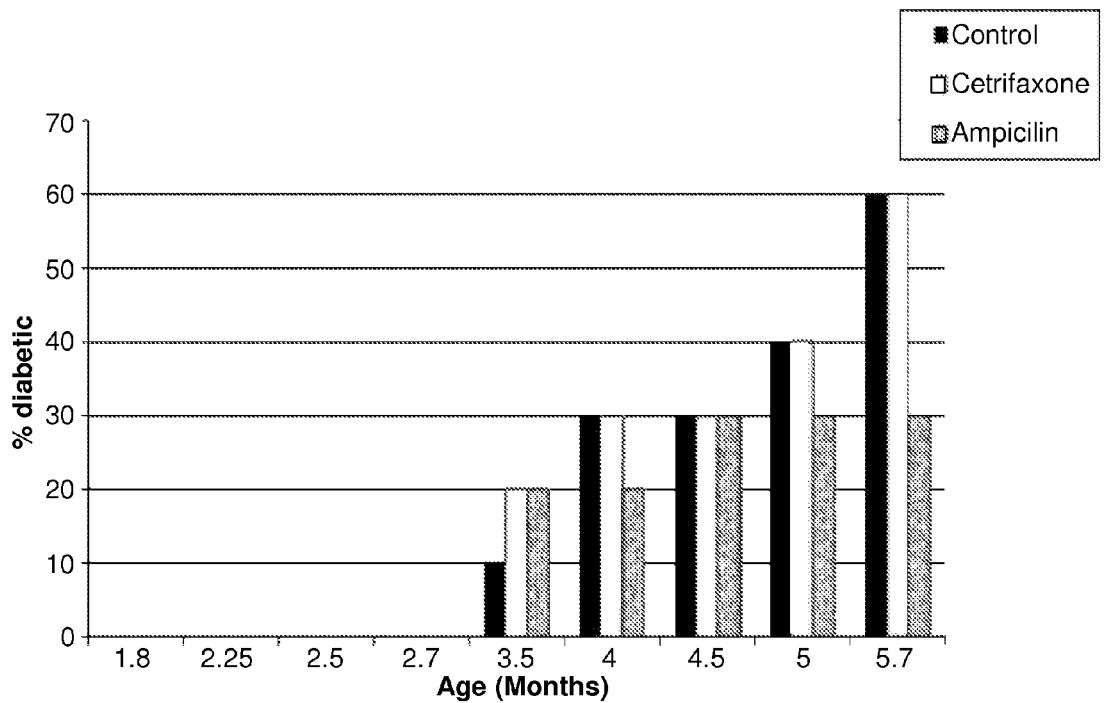

NOD mice spontaneously develop diabetes mellitus similar to type I diabetes in humans. Since ceftriaxone enhanced EAE, but ampicillin did not, the effects of the two beta-lactam antibiotics on the development of autoimmune diabetes in NOD mice was tested. Groups of 10 mice were untreated or injected subcutaneously at weekly intervals (in contrast to antibiotic treatment regime which is 3 daily intravenous injections) with either ceftriaxone (675 µg per mouse) or ampicillin (at a dose of 1300 µg per mouse). The mice were followed for the development of diabetes, marked by blood sugar above 300 mg/dl on 2 measurements. The mice treated with ampicillin developed an incidence of diabetes of 30% at 5.7 months; while the control and ceftriaxone-injected mice manifested a 60% incidence of disease (FIG. 1D; P=0.05 control versus ampicillin and p=0.017 ceftriaxone versus ampicillin). Thus, some beta-lactam antibiotics can have opposing effects on different T-cell mediated autoimmune diseases in rodents: ampicillin down-regulates NOD mouse diabetes, but not rat EAE, and ceftriaxone up-regulates rat EAE, but not mouse diabetes.

Example 5

Cefuroxime and Ampicillin Manifest Opposing Effects on Immune-Related Gene Expression in Human T Cells The Human Autoimmune and Inflammatory Response Gene Array (SuperArray Bioscience corporation, Frederick, Md., USA) was used for analysis of gene expression by the T cells. This array contains 367 genes including cytokines, chemokines and their receptors, transcription factors and signaling proteins. CD4+ T cells were purified from healthy human donors, stimulated for 120 min with mitogenic plate-bound anti-CD3 antibody in the presence or absence of cefuroxime (Cef.) 50 μg/ml or ampicillin (Amp.) 50 μg/ml, and the effect on gene expression was analyzed. Analysis of the results was performed using the GEArray analysis program (www.SuperArray.com). The results are shown in Table 1 hereinbelow. Fifty-seven genes were found to be down-regulated by cefuroxime ("Cef"); but most of these genes (56 of the 57) were up-regulated by ampicillin ("Amp"). Interestingly, 8 of these genes were reported to be down-regulated in the peripheral blood lymphocytes of multiple sclerosis patients in Israel (Achiron et al. (2004) Ann Neurol, 55, 410-417), and 15 of these genes were down-regulated in the T cells of Japanese multiple sclerosis patients (Satoh et al. (2006) J Neuroimmunol, 174, 108-118). The products of these genes included cytokines, chemokines and their receptors, signaling molecules and transcription factors (Table 1). Many of the genes down-regulated by cefuroxime and up-regulated by ampicillin were reported to participate in Th2 and Treg pathways, and only a minority have been implicated in the Th1 pathway. It should be noted that the cytokine gene TNFα, considered to be pro-inflammatory, was found to have anti-inflammatory effects in knockout mice (Liu et al. (1998) Nat Med, 4, 78-83). The down-regulation of molecules in the Th2/Treg pathways by cefuroxime is consistent with its augmentation of EAE (Garren et al. (2001) Immunity, 15, 15-22) and AA (Mimran et al. (2004) J Clin Invest, 113, 924-932); in contrast, the up-regulation of these genes by ampicillin is consistent with its down-regulation of NOD diabetes (Elias et al. (1997) Diabetes, 46, 758-764). To verify the results detected by the gene array study, a panel of six genes was designed and tested by real-time PCR: CCR4, ACVR2, JAK1, STAT4, TLR2 and NFKBIE. The cDNA that was used was prepared from the same RNA used for the gene array experiment. The real-time PCR showed that each of the six genes that were down-regulated in the gene-array experiment by cefuroxime treatment were suppressed by cefuroxime treatment in the RT-PCR experiment.

TABLE 1

Effects of cefuroxime and ampicillin on gene expression by CD4+ human T cells

| Gene | Full name/Description | Reported to be decreased in MS patients | % decrease[1] by Cef. | % increase by Amp. | Function[2] | Th1/Th2[3] |
|---|---|---|---|---|---|---|
| Chemokines, cytokines and their receptors | | | | | | |
| CCR4 | Chemokine receptor 4 | Satoh et al. 2006 CCR5 | 39 ± 2 | +31 | Chemokine receptor | Expressed on Th2 cells and on diabetogenic Th1 cells |
| CCR6 | Chemokine receptor 6 | | 53 ± 5.6 | +83 | Chemokine receptor | Expressed on T-regulatory |
| CCR7 | Chemokine receptor 7 | Satoh et al. 2006 CCR5 | 38 ± 8.1 | +43 | Binds CCL21 | Expressed in EAE |
| CCL5 | Chemokine ligand 5 | | 21 ± 5.6 | +25 | Chemo-attractant for monocyte memory T cells eosinophil | Expressed in EAE lesion |
| CXCL10 | Chemokine 10 | | 39 ± 3 | +25 | CXCR3 - the receptor Attracts Th1 cells | Antibody to CXCL10 exacerbates EAE Anti body to CXCL10 protects from EAE, DM |
| LTA | Lympho-toxin alpha | | 17 ± 10 | +48.5 | Cytokine | Blocking of LTA exacerbates Arthritis, Th1 |
| TNFα | Tumor necrosis factor alpha | Achiron et al. 2004 | 29 ± 8.5 | +39 | Cytokine | Th1, k/o mice show severe EAE |
| CCL11 | Chemokine ligand 11 | | 18 ± 6.6 | +107 | Cytokine Eotaxin, binds CCR3 | Th2, attracts eosinophils |

TABLE 1-continued

Effects of cefuroxime and ampicillin on gene expression by CD4+ human T cells

| Gene | Full name/ Description | Reported to be decreased in MS patients | % decrease[1] by Cef. | % increase by Amp. | Function[2] | Th1/Th2[3] |
|---|---|---|---|---|---|---|
| SDF2 | Stromal cell derived fact | | 28 ± 12 | +71 | Secreted | unknown |
| IL16 | Interleukin 16 | Satoh et al. 2006 | 50 ± 7.8 | +14 A low expression | Lymphocyte chemo-attractant factor | Th2 |
| IL1B | Interleukin-1 beta | Achiron et al. 2004 | 54 ± 7.0 | +64 A low expression | Cytokine | Pro-inflammatory |
| IL9R | Interleukin 9 receptor | | 27.5 ± 3 | No change | receptor | Th2 |
| TNFRSF11A | Tumor necrosis factor receptor superfamily, member 11a | Achiron et al. 2004 Satoh et al. 2006 | 43 ± 2 | +81 A low expression | Membranal Activator of NFKB | unknown |
| IL2RB | Interleukin-2 receptor subunit beta | Satoh et al. 2006 | 50 ± 9.9 | +93 | Surface Binds IL2 | |
| IL2RG | Interleukin-2 receptor gamma | Satoh et al. 2006 | 57 ± 9.8 | +78 A low expression | Receptor | unknown |
| Surface receptors | | | | | | |
| TLR2 | Toll-like receptor 2 | | 52 ± 14 | +419 A low expression | Receptor | EAE Expression in Treg |
| CD28 | | | 51 ± 2.1 | +175 | Surface Binds B7-1 | Th2 |
| SELL | Selectin L | Satoh et al. 2006 | 46 ± 7.0 | +124 | Adhesion to High endothelial venules (HEV) | Th1 (unknown) |
| TGFβ related | | | | | | |
| ACVR2 | Activin receptor II | | 60 ± 14.8 | +85 A low expression | Activin is TGFbeta like | |
| ACVR1 | Activin receptor I | | 42 ± 0.7 | +53 A low expression | Activin is TGFbeta like | |
| TGIF | Trans-forming growth-interacting factor | | 43 ± 3.5 | +72 A low expression | Transcription Factor represses SMAD2,3 | Anti Th2 |
| TGFBR3 | Trans-forming growth factor beta receptor III | Satoh et al. 2006 TGFBR1,2 | 44 ± 3.5 | +139 | Receptor | Regulatory |
| SMAD7 | | | 47 ± 4.2 | +34 A low expression | Inhibits TGFb | |
| SMAD4 | TGFb signal transduction pathways | Satoh et al. 2006 | 47 ± 7.0 | +85 | TGFb signal transduction pathways | Th3 |
| Kinases, signal transduction | | | | | | |
| MAP3K2 | Mitogen-activated protein 3kinase 2 | | 36 ± 12 | +93 | Regulates JNK ERK5 | unknown |
| MAP3K7 | Mitogen-activated protein 3kinase 7 | Satoh et al. 2006 | 46 ± 9.9 | +124 | TGFb signaling NfKB activation p38 MAPK | unknown |

TABLE 1-continued

Effects of cefuroxime and ampicillin on gene expression by CD4+ human T cells

| Gene | Full name/ Description | Reported to be decreased in MS patients | % decrease[1] by Cef. | % increase by Amp. | Function[2] | Th1/Th2[3] |
|---|---|---|---|---|---|---|
| MAP3K1 | Mitogen-activated protein 3kinase 1 | Achiron et al. 2004 | 53 ± 12 | +63 A low expression | Activates ERK JNK | unknown |
| MAP2K4 | Mitogen-activated protein 2kinase 4 | Satoh et al. 2006 MAP2K1 | 52 ± 14.1 | +150 | | Th1 (unknown) |
| MAPK9 | Mitogen-activated protein kinase 9 | Achiron et al. 2004 | 42 ± 10.9 | +46 | JNK2 | Th1 (unknown) −/− No effect on EAE |
| PAK1 | Protein kinase 1 | Satoh et al. 2006 PAK2 | 40 ± 2.4 | +111 | JNK Apoptosis | unknown |
| IRAK1 | Interleukin-1 receptor-associated kinase 1 | | 44 ± 2.1 | +171 | | Th1 IL10 |
| JAK1 | Janus kinase 1 | Satoh et al. 2006 | 53 ± 13.4 | +161 | Interferon α β γ transduction | Th1 and IL4 |
| Transcription factors | | | | | | |
| NFKB1 | Nuclear factor kappa-B 1 | Achiron et al. 2004 | 43 ± 3.5 | +31 | Transcription Factor | Inhibits NFKB Th2 |
| NFKB2 | Nuclear factor kappa-B 2 | Achiron et al. 2004 Satoh et al. 2006 increased | 53 ± 10.6 | +195 | Transcription factor lymphoma | unknown |
| NFKBIL1 | Nuclear factor-kappa-B inhibitor-like protein 1 | | 54 ± 12.5 | +191 | Transcription factor | unknown |
| NFKBIE | Nuclear factor of kappa light polypeptide gene enhancer in B-cells inhibitor, epsilon | Satoh et al. 2006 increased | 63 ± 11 | +132 | Inhibits NfkB | Th2 |
| SRF | Serum response factor | | 38 ± 1.9 | +58 | Transcription factor | unknown |
| EGR3 | Early growth response3 | | 38 ± 2.8 | −25 | Transcription factor | Mitogenic activation induced in T cells, FAS-L expression |
| JUN | | Satoh et al. 2006 | 49 ± 2.2 | +65 | Interacts with c-fos to form a dimer. Interacts with smad3/smad4 heterodimer | Th2 (unknown) |
| RFXAP | Regulatory factor X-associated protein | | 27 ± 12 | +131 | MHCII expression | unknown |
| CREB1 | Cyclic AMP responsive element binding protein 1 | Satoh et al. 2006 | 19 ± 4.9 | +101 | Transcription factor | unknown |

TABLE 1-continued

Effects of cefuroxime and ampicillin on gene expression by CD4+ human T cells

| Gene | Full name/ Description | Reported to be decreased in MS patients | % decrease[1] by Cef. | % increase by Amp. | Function[2] | Th1/Th2[3] |
|---|---|---|---|---|---|---|
| YY1 | Yin yang 1 | | 23 ± 9.1 | +152 | Transcription factor | Th2 activates IL4 |
| REL | | | 45 ± 1.9 | +132 | Transcription factor | Th1 IL12 |
| TRAF6 | TNF receptor associated factor 6 | Achiron et al. 2004 | 43 ± 3.5 | +39 A low expression | NfkB and JNK activation | Limit Th2 |
| TRAF5 | TNF receptor associated factor 5 | | 43 ± 2.2 | +47 A low expression | | Limit Th2 |
| STAT1 | Signal transducer and activator of transcription 1 | Satoh et al. 2006 | 32 ± 11 | +85 | Transcription factor | Reg T Th1 |
| RFX5 | Regulatory factor X, 5 | | 36 ± 4.2 | +137 | MHCII expression | |
| STAT4 | Signal transducer and activator of transcription 4 | | 47 ± 9.3 | +11 | Transcription factor | Th1 Th2 |
| SP3 | | | 39 ± 9.9 | +47 | Transcription factor IL10 control | Th2 (unknown) |
| STAT6 | Signal transducer and activator of transcription 6 | | 47 ± 7.9 | no change | Transcription factor | Th2 IL4 |
| GFI1 | Growth factor independ1 | | 45 ± 14 | +10 | Transcription factor | Anti inflammatory |
| Others | | | | | | |
| CD40LG | CD40 ligand | | 33 ± 7.1 | +67 | Surface B cell interaction | Required for EAU Autoimmune disease |
| RANBP5 | Importin beta3 | | 33 ± 3.5 | +108 | Nuclear proteins transport | unknown |
| ACTB | Actin beta | | 49 ± 11 | +196 | | |
| HRAS | | Satoh et al. 2006 | 30 ± 9.8 | −12 A low expression | Oncogene | unknown |
| CREBBP | CREB-binding protein | | 40 ± 9.9 | +49 | Acetylates nuclear proteins | |
| PIN1 | Peptidyl-prolyl cis-trans isomerase NIMA-interacting 1 | | 45 ± 12.1 | +105 | Isomerase | unknown |

[1]Percent decrease ±Standard deviation in cefuroxime treated human CD4+ T cells relative to control
[2]Cellular function of the gene as found in databases
[3]Based on articles linking suggested gene to TH1, Th2 or Treg pathways. Data on some genes supported evidence linking the gene to more than one pathway (for example: CCR4, CXCL10). "unknown" indicates unknown function in Th1/2 polarization.

Example 6

A Human T-Cell Protein of 67 kDa Specifically Binds Penicillin Covalently

Figure 2A:
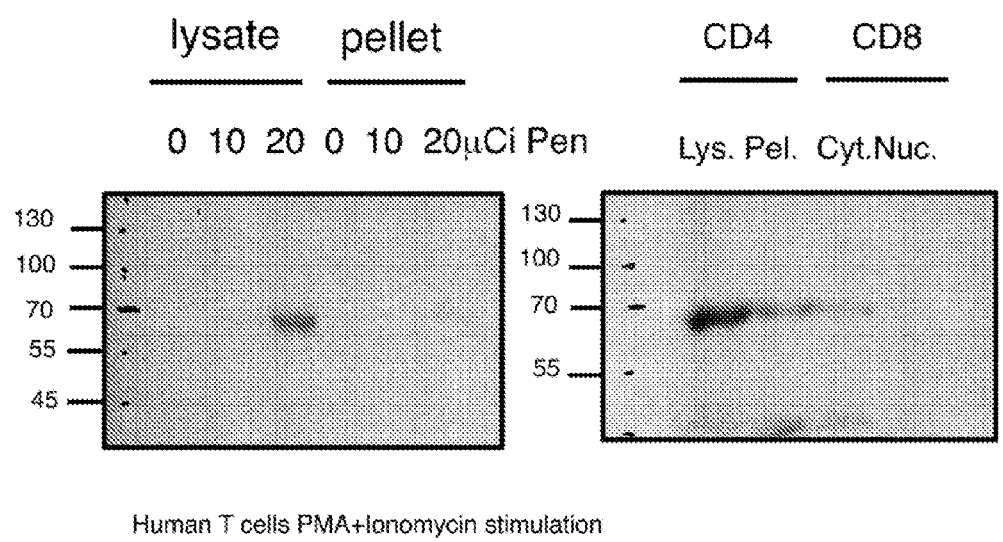
FIG. 2. A) Radioactively labeled penicillin binds to a 67 kDa band in human T-cell lysates. Left panel: CD4 T cells, right panel CD4 and CD8 T cells. Lys. signifies total lysate; Pel. pellet of total lysate; Cyt. Cytoplasmic; and Nuc. nuclear fraction. B) Results of the mass spectrometry report on the 67 kDa band.

Penicillin and other beta-lactam antibiotics have been shown to inhibit bacterial cell-wall synthesis by binding covalently to specific penicillin-binding proteins and thus interfere with their enzymatic activity. To test whether beta-lactam antibiotics might affect T-cell behavior likewise by covalently binding a key T-cell protein, purified CD4 or CD8 human T cells were incubated with 10 and 20 µCi of tritium-labeled lactam benzylpenicillin (Amersham, Buckinghamshire, UK) for 3 days during stimulation with PMA and Ionomycin. The stimulated T cells were collected, washed, lysed and their proteins were subjected to SDS-PAGE separation. Dried gels were exposed in intensifying screens to Xray film for 2 weeks at −80° C. As can be seen in FIG. 2A, a single major penicillin-protein radioactive band was detected at 67 kD in lysates of both CD4 and CD8 T cells. The intensity of the band was stronger at the 20 µCi concentration of penicillin.

Example 7

Identification of the 67 kD Penicillin-Binding Band as Albumin

The 67 kD lactam-binding band was isolated by activating human T cells in the presence of biotinylated ampicillin or biotinylated ceftriaxone. The cells were lysed and the lysates were purified by binding to a captavidin column (Invitrogen, Carlsbad, Calif. USA). The fractions binding the beta-lactam antibiotics were eluted by applying carbonatebicarbonate buffer or by free biotin. The isolated protein band was subjected to enzymatic digestion and the resulting peptides were identified by mass spectrometry. The 67kD protein from human CD4 T cells was identified as human serum albumin (FIG. 2B, SEQ ID NO: 19). Thus albumin seems to be a lactam-binding protein in human T cells.

Figure 3A:
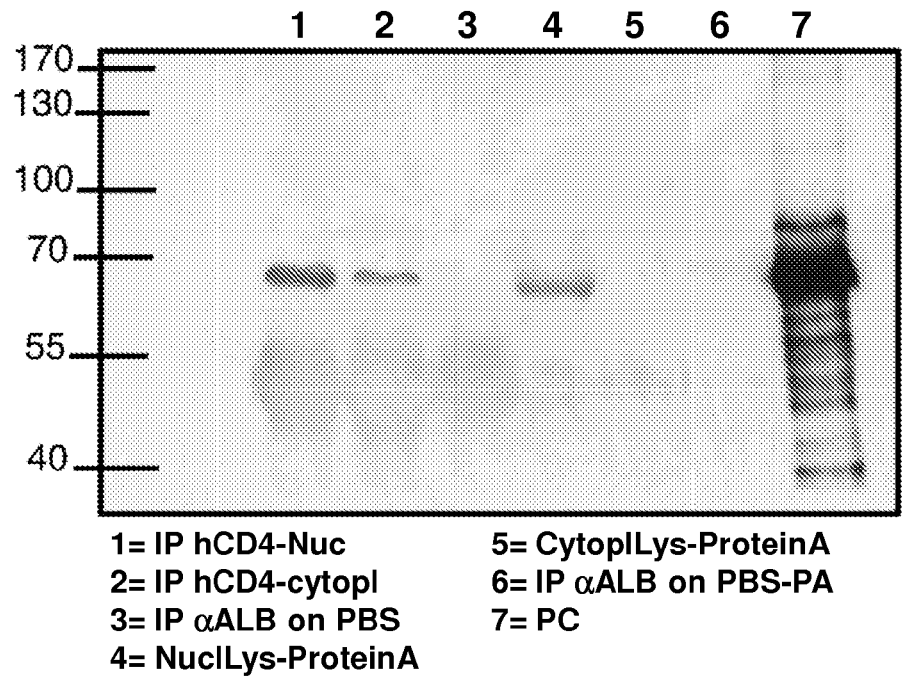
FIG. 3. A) Immunoprecipitation of 67 kDa band molecule by an anti-human serum albumin antibody. B) T cells express albumin modifiable by penicillin. The Pen 9-labelled 67 kD band is present only in penicillin-treated T cells. Abbreviation: Pen-penicillin, Amp-ampicillin, Zin-zinacef-cefuroxime, Chlor-chloramphenicol, Vanc-vancomycin.

As albumin is a known contaminant in sequencing studies, the isolation of the 67 kD band from penicillin-treated cells was repeated using immuno-precipitation (IP) with anti-human serum albumin (anti-has, αALB). Cytoplasmic or nuclear lysates of human CD4 T cells treated with penicillin were incubated with rabbit polyclonal anti-human albumin (Sigma), precipitated with protein A sepharose and run in an SDS gel. Lysates without the protein A-bound complex (collected after the immunoprecipitation) were run as controls. Western blotting was then performed with an antibody that binds specifically to penicillin bound to proteins—pen 9 (de Haan et al. (1985) *Int Arch Allergy Appl Immunol*, 76, 42-46). FIG. 3A shows the results of this experiment. The 67 kD band appears in the IP of cytoplasmic ("IP hCD4-cytopl") and nuclear ("IP hCD4-Nuc") fractions; the band is absent from a lysate of the cytoplasmic fraction collected after the immunoprecipitation ("CytoplLys-ProteinA", lane 5). In other words, IP with anti-HSA antibody resulted in the disappearance of the penicillin-protein band from the cytoplasmic lysate, suggesting that except for albumin there are no other proteins of a similar molecular weight that are modified by penicillin.

Example 8

Figure 3B:
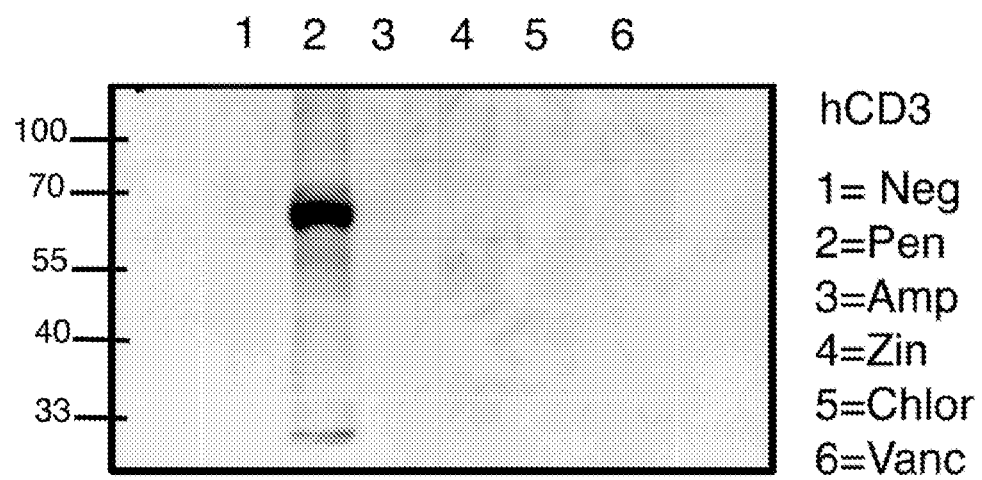

Analysis of T-Cell Beta-Lactam Binding by Anti-Penicilloyl-Albumin Antibody A monoclonal anti-penicilloyl-albumin antibody was used to further confirm that the beta-lactam binding molecule produced by human T cells is albumin. When penicillin binds covalently to a protein, the beta-lactam ring binds to a lysine residue. A monoclonal antibody called Pen 9 is specific to the thiazolidine ring of penicillin bound to albumin (de Haan et al. (1985), as above). To test the reactivity of Pen 9 in the present system, purified human T cells were activated by mitogenic treatment in the presence of the beta-lactam antibiotics penicillin and ampicillin or with other families of antibiotics in culture, and the lysates were tested by western blot with Pen 9. FIG. 3B shows that the Pen 9 reacted specifically to a major protein of the penicillin-treated T cells and not to any other antibiotic in human CD3 T cells. It should be noted that Pen 9 did not bind to the ampicillin-treated T cells; apparently the albumin molecule modified by ampicillin does not present the specific epitope presented by the penicillin-albumin molecule.

Example 9

Pen 9 Monoclonal Antibody Detects Penicillin-Albumin In Vivo

Figure 4A:
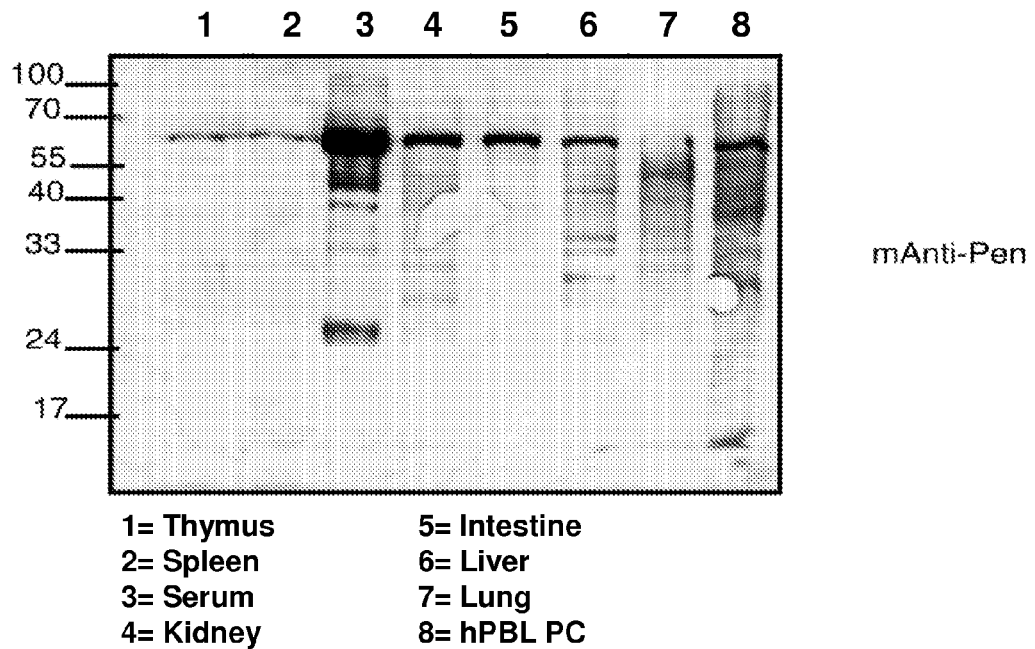
FIG. 4. A) Detection of in vivo penicillin-labelled proteins. The 67 kD band is present in all tissues and is most abundant in serum sample. B) Western blot analysis of various cell lines treated with penicillin shows the dominant 67 kDa band in most samples.
Figure 4B:
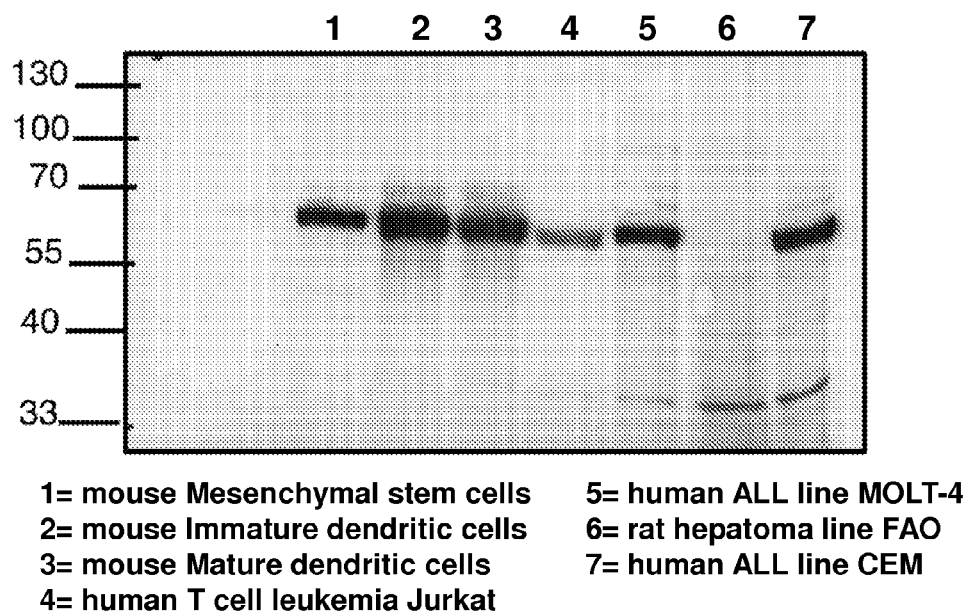

To learn whether penicillin binds albumin in vivo, Lewis rats were injected intraperitoneally with penicillin G (50 mg/rat) and 2 hours later various tissue lysates were tested for reactivity with pen 9 antibody in western blot. The results are shown in FIG. 4A. The 67 kD band representing penicilloylated albumin appears in all tissues examined and is most abundant in serum. Lysates of various cell lines raised in vitro were also tested. FIG. 4B shows that the penicillin-modified albumin band could be detected in mesenchymal stem cells, dendritic cells, Jurkat, MOLT4, FAO and CEM lines. Albumin was absent in the FAO rat hepatoma cell line that is known to have dedifferentiated and to have lost its expression of albumin (Cairo et al. *Exp Cell Res*, 206, 255-260).

Example 10

Albumin mRNA is Expressed by T Cells

Figure 5:
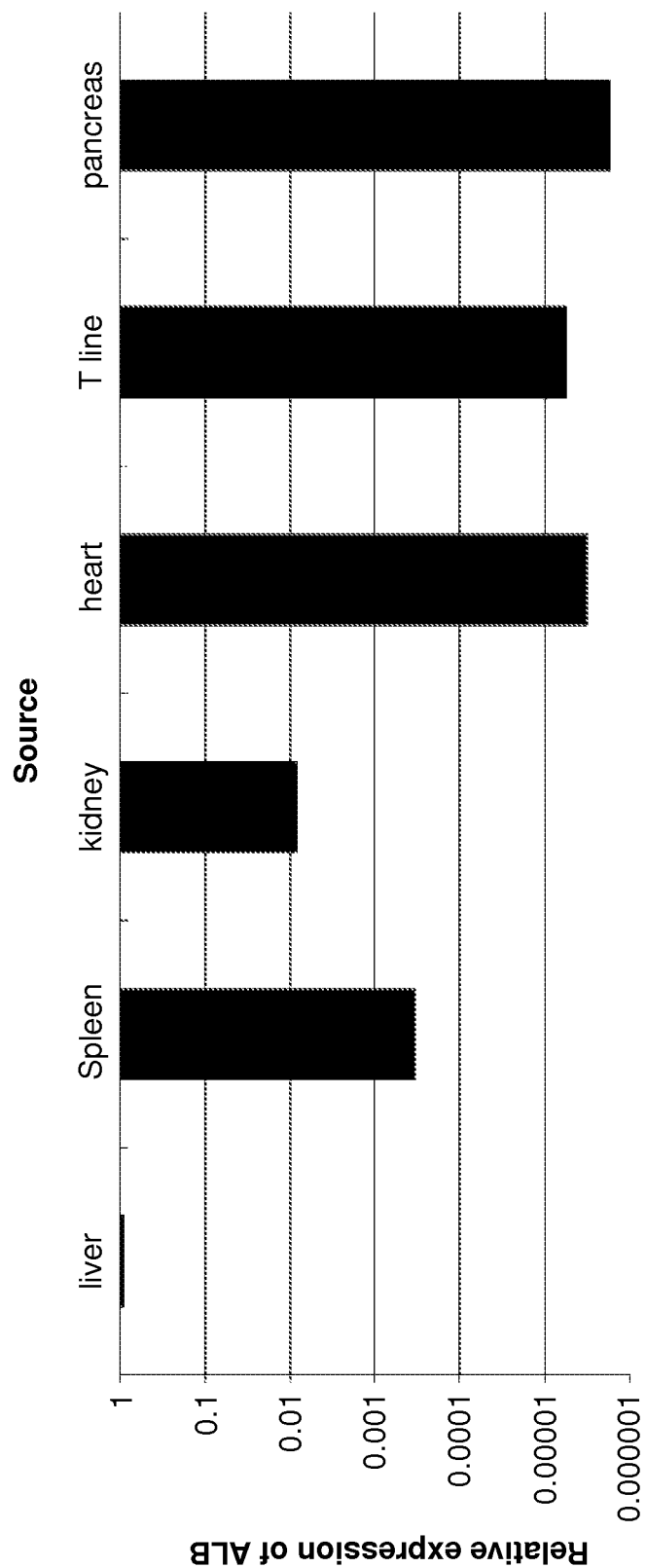
FIG. 5. Relative expression of albumin mRNA in various tissues by RT-PCR.

To test whether T cells might indeed produce albumin, the expression of albumin mRNA in rat T cells compared to other tissues was analyzed by RT-PCR. Total RNA was extracted from various tissues and cDNA was prepared. RT-PCR was performed and the quantities relative to liver were depicted. FIG. 5 shows that albumin mRNA could be detected in rat T cells, as well as in spleen, kidney, heart and pancreas. A similar level of expression was detected in human CD4 T cells.

Example 11

Penicillin-Modified Albumin is Taken Up by T Cells

Figure 6A:
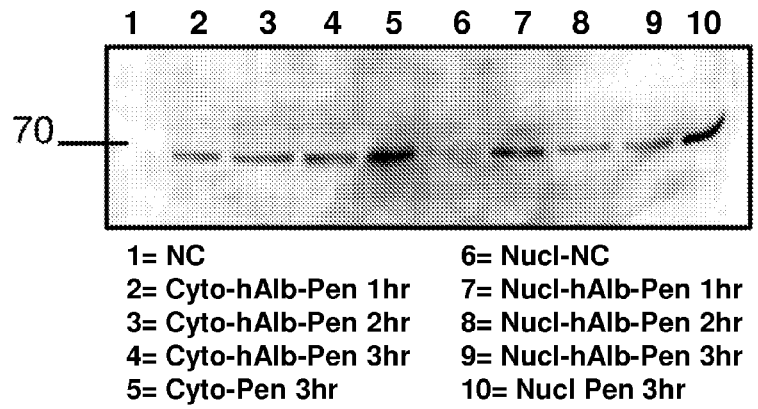
FIG. 6. A) Western blot of human CD4 T cells incubated with Penicillin-modified albumin. B) Penicillin-modified albumin augments the pathogenicity of BP10 line.

To test whether penicillin-modified albumin can enter T cells, human serum albumin was incubated with penicillin, and then dialysed extensively. The resulting penicillin-modified-albumin was incubated with purified human CD4 T cells for 3 hours, and the cells were lysed and tested by western blot with monoclonal Pen 9 antibody. T cells were harvested after 1, 2, or 3 hrs. Cytoplasmic ("Cyto") and nuclear ("Nucl") fractions were run on SDS transferred to nitrocellulose and tested with Pen 9 antibody. FIG. 6A shows the results. The penicillin-modified albumin ("hAlb") detected by Pen 9 entered the cells and was detectable in the nuclei within 1 hr. Cytoplasmic and nuclear penicillin-labeled-albumin was seen after 1 hr, and peaked at 3 hr. In additional experiments, it was found that nuclear entry of the penicillin-modified albumin was augmented upon T cell activation for 1 hr with PMA and Ionomycin. Thus, T cells, both in the resting and activated states, can take up penicillin-modified albumin and transport it to the nucleus.

Example 12

Penicillin-Modified Albumin Augments the Pathogenicity of the BP10 Line

Figure 6B:
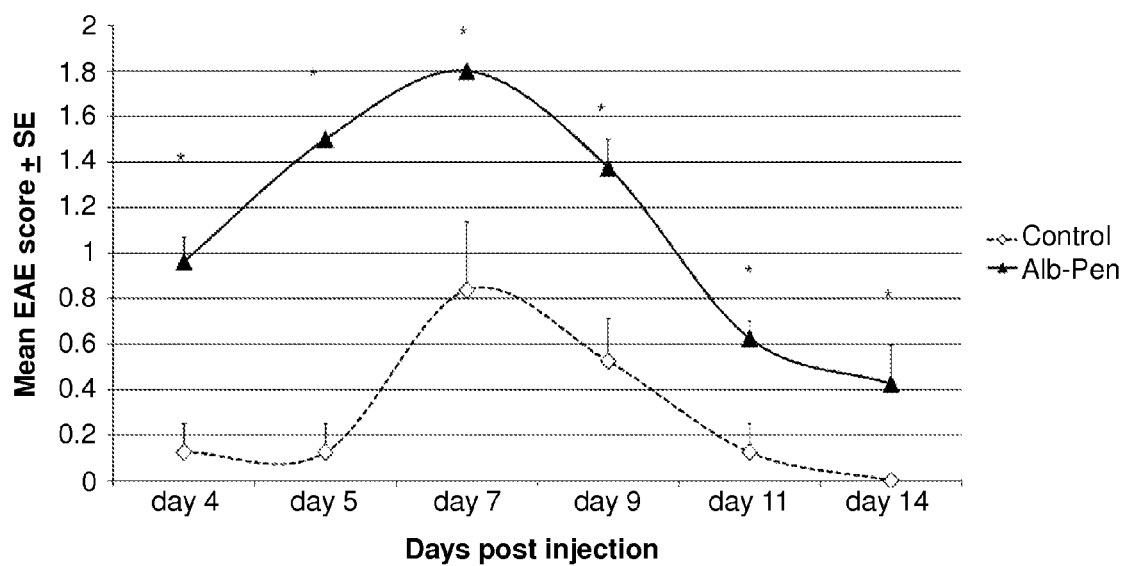

To test whether the penicillin-modified albumin moiety itself could enhance the effector functions of a T-cell line, the encephalitogenic BP 10 line was stimulated with penicillin-modified albumin (at 5 mg/ml) for 3 days in stimulation medium and tested in vivo the capacity of the line to mediate EAE (human albumin was incubated or not with penicillin (100 mg/ml for 2 hrs at 37° C.), dialysed against PBS, and then added at 5 mg/ml to stimulation medium of BP10 line). A control group was injected with the untreated line. FIG. 6B shows that similar to penicillin alone, penicillin-modified albumin enhanced the pathogenicity of the T cells. Penicillin-modified rat albumin ("Alb-Pen") could also enhance the encephalogenicity of the BP10 line. In additional experiments, unmodified human albumin alone had no significant effect on the severity of the EAE mediated by the line.

Example 13

Beta-Lactam Compounds Devoid of Anti-Bacterial Activity can Also Enhance EAE

The following beta-lactam compounds were tested for their influence on the severity of adoptive EAE, in parallel to the conventional beta-lactam antibiotics: clavulanic acid, 6-aminopenicillanic acid (6-APA) and tazobactam (from Sigma). These compounds do not have antibiotic activity (do not kill bacteria directly).

Figure 7A:
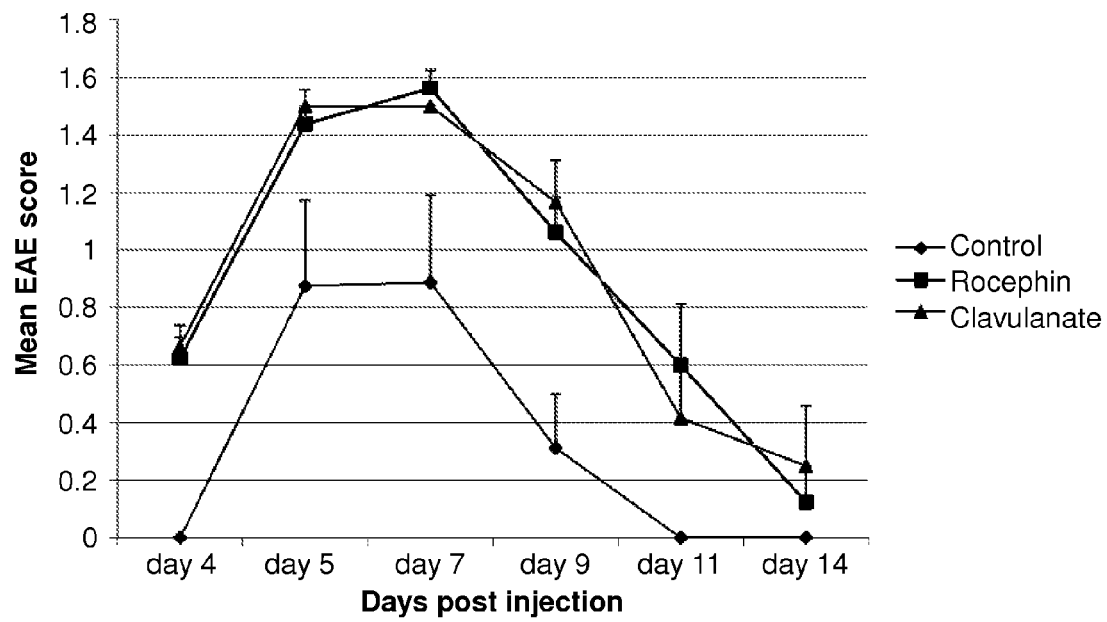
FIG. 7. Enhancement of EAE by beta-lactam compounds devoid of anti-bacterial activity. A) Clavulanic acid. B) 6-APA and tazobactam.

1. Clavulanic acid: BP10 line was stimulated with clavulanic acid (25 µg/ml) or ceftriaxone (Rocephin), the cells were injected into recipient rats (5 rats per group), and EAE score in these rates was tested. The concentration of clavulanic acid used in stimulation was determined after testing the dose response curve of several concentrations on BP10 line stimulation. As can be seen in FIG. 7A, clavulanic acid at 25 µg/ml in the stimulation medium enhanced the pathogenicity of BP10 line similar to ceftriaxone (Rocephin).

Figure 7B:
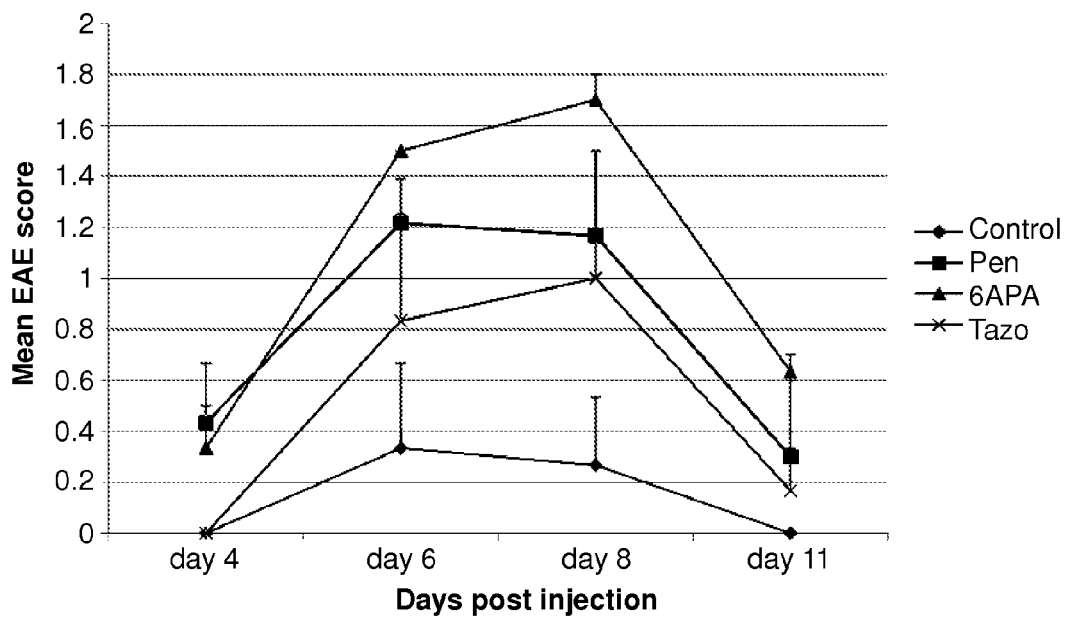

2. 6-APA and tazobactam: 6-APA is an intermediate in the synthesis of semi-synthetic penicillins, available commercially (Sigma). Tazobactam is a beta lactamase inhibitor, similar to clavulanic acid. The influence of these two compounds on EAE was tested as described above in comparison to penicillin, for the same doses. As can be seen in FIG. 7B, both compounds had an EAE enhancing ability, similar to penicillin.

Example 14

Inhibition of Tumor Growth by Beta-Lactam Compounds in RMA Mouse Tumor Model

Figure 8A:
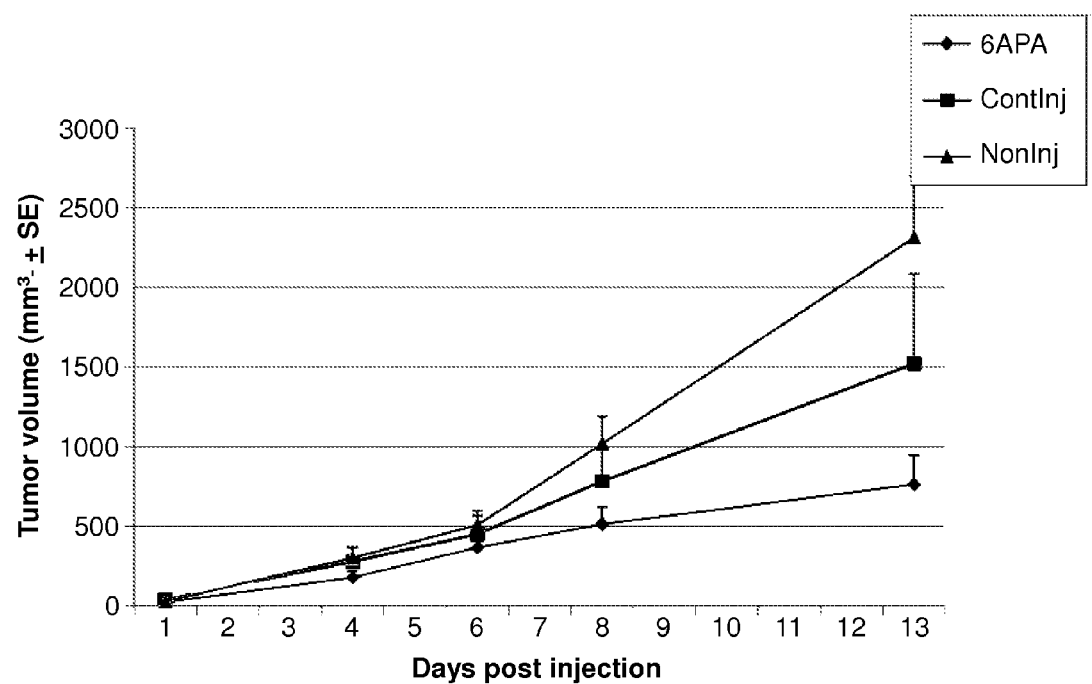
FIG. 8. Inhibition of tumor growth by beta-lactam compounds in RMA mouse tumor model. A) 6-APA. B) 6-APA and clavulanic acid.

In the RMA mouse tumor model (T cell lymphoma of mouse origin), T cells are known to participate in tumor rejection, and thus augmenting T cell effects might enhance the animal's ability to reject the tumor implant. RMA cells were injected to C57BL/6J Ola Hsd mice ($10^5$ cells per mouse) (Chen et al. (1994) *J Exp Med,* 179:523-532). Three groups of mice were used (10 mice per group): experimental group ("6APA"), which was given SC 6-APA (2 µg/mouse) 3 times per week, a first control group ("ContInj") that was given the solution used for dissolving 6-APA (which is difficult to dissolve in aqueous solution), and a second control group ("NonInj") that did not receive any treatment (non-injected). Tumor size was measured and recorded. As can be seen in FIG. 8A, tumors were significantly smaller in mice treated with 6-APA as compared to control mice at the last two measurements.

Figure 8B:
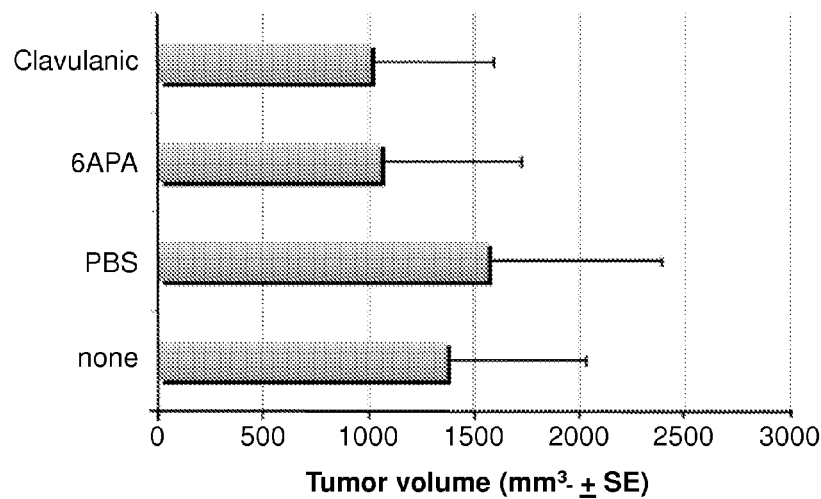

An additional experiment was carried out in the same experimental system, comparing 6-APA to clavulanic acid. FIG. 8B shows the results of tumor measurements in mice 17 days after tumor injection. As can be seen in the figure, both groups of beta lactam treated mice had smaller tumors by day 17 post inoculation as compared to PBS treated and non-injected mice.

Example 15

Effect of Beta-Lactam Compounds (Antibiotics and Non-Antibiotics) on 3LL Tumor Model Similar analysis was performed using the 3LL mouse tumor model (Lewis lung carcinoma-highly metastatic clone D122), for which tumor rejection is also immune mediated (Li et al. (2001) *J Immunother,* 24:472-481; and Gorelik et al. (1980) *J Natl Cancer Inst,* 65:1257-1264). C57B1 mice (10 per group) were injected with D122 cells IV ($10^5$ cells per mouse). The mice were treated intraperitoneally, 3 times per week, with one of the following beta-lactam compounds: clavulanic acid ("Clav"), 6-APA, tazobactam ("Tazo") and ceftriaxone ("Roc"). The control groups included PBS treated mice, untreated mice and normal mice. After 6 weeks (when part of control mice were dead from lung metastases), mice were sacrificed and lung weight (reflecting metastatic load) was measured.

Figure 9A:
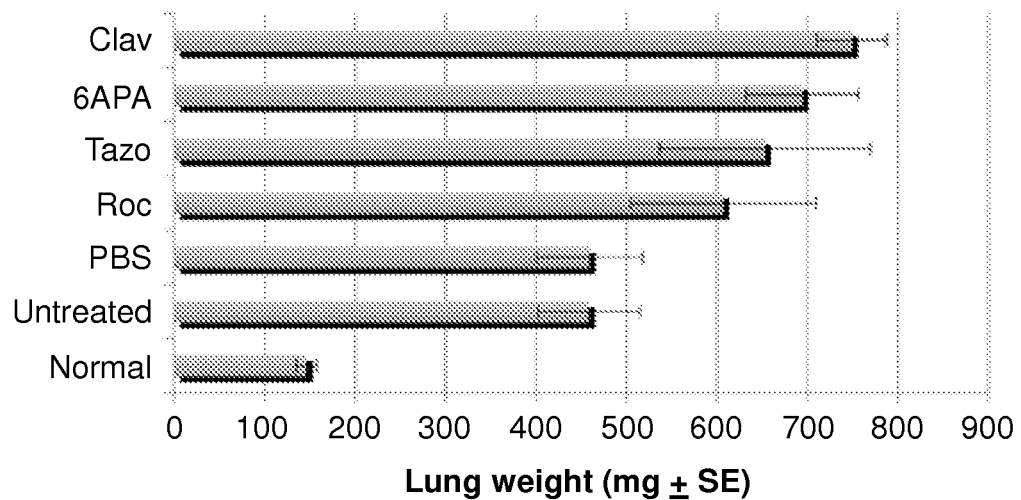
FIG. 9. Effect of beta-lactam compounds on 3LL mouse tumor model. A) Effect on lung-weight. B) Effect on mice survival.
Figure 9B:
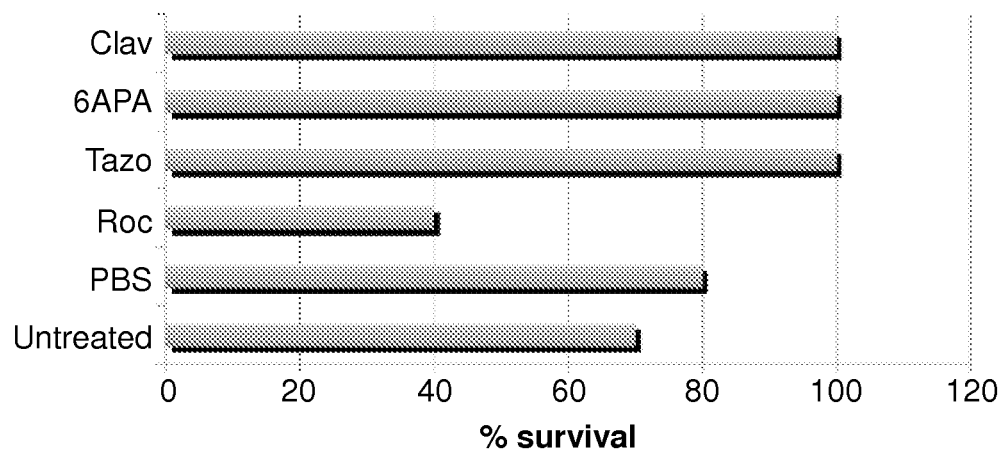

The results are shown in FIG. 9A. As can be seen in the figure, treated mice had higher lung weights. However, when the survival of mice is plotted (FIG. 9B), the treated mice had a better survival, despite an increase in lung volumes.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for enhancing a T-cell-mediated immune response in a subject, the method comprising:
    (i) incubating T cells collected from the subject with a beta-lactam compound capable of enhancing T cell activity, or a salt thereof, wherein the beta-lactam compound is selected from the group consisting of:
        (a) a beta-lactam antibiotic selected from cefuroxime, benzylpenicillin, phenoxymethylpenicillin, and ceftriaxone, said beta-lactam antibiotic is at a concentration ranging from about 20 µg/ml to about 55 µg/ml, and (b) a beta-lactam compound devoid of antibacterial activity selected from clavulanic acid, 6-aminopenicillanic acid (6-APA), and tazobactam, said beta-lactam compound devoid of antibacterial activity is at a concentration of at least 25 µg/ml, thereby obtaining stimulated T cells; and
    (ii) re-infusing said stimulated T cells to said subject.

2. The method of claim 1, wherein the T-cell-mediated immune response is a T-cell mediated anti-tumor response.

3. The method of claim 1, wherein the method is utilized for the treatment of a viral infection.

4. The method of claim 1, wherein the method is utilized for the treatment of a parasitic infection.

5. The method of claim 1, wherein the subject is selected from a human and a non-human mammal.

6. The method of claim 1, wherein step (i) comprises incubating the T cells with a plurality of beta-lactam compounds capable of enhancing T cell activity.

7. The method of claim 1, wherein step (i) further comprises at least one of mitogen activation of the T cells and antigen-specific activation of the T cells.

8. The method of claim 7, wherein the antigen is a tumor antigen.

9. The method of claim 1, wherein the T cells are T cells from peripheral blood of the subject.

10. The method of claim 1, wherein the T cells are tumor-infiltrating T cells.

11. A method for enhancing a T-cell-mediated immune response in a subject, the method comprising:
    (i) incubating T cells collected from the subject with a beta-lactam compound capable of enhancing T cell activity conjugated to albumin, wherein the beta-lactam compound is selected from the group consisting of cefuroxime, benzylpenicillin, phenoxymethylpenicillin, ceftriaxone, clavulanic acid, 6-aminopenicillanic acid (6-APA) and tazobactam, thereby obtaining stimulated T cells; and
    (ii) re-infusing said stimulated T cells to said subject.

12. The method of claim 11, wherein the albumin is human serum albumin.

* * * * *